US011915811B2

(12) United States Patent
Keenan et al.

(10) Patent No.: US 11,915,811 B2
(45) Date of Patent: Feb. 27, 2024

(54) SYSTEM AND METHOD FOR DETERMINING AN APPROPRIATE DOSE OF A PRODUCT

(71) Applicant: GOFIRE, INC., Denver, CO (US)

(72) Inventors: Joseph Francis Keenan, Superior, CO (US); John Jesse Woodbine, Lafayette, CO (US); Peter William Calfee, Denver, CO (US)

(73) Assignee: Kaival Labs, Inc., Grant-Valkaria, FL (US)

( * ) Notice: Subject to any disclaimer, the term of this patent is extended or adjusted under 35 U.S.C. 154(b) by 530 days.

(21) Appl. No.: 16/559,556

(22) Filed: Sep. 3, 2019

(65) Prior Publication Data

US 2021/0065860 A1    Mar. 4, 2021

(51) Int. Cl.
    *G16H 20/10*    (2018.01)
    *G06F 16/2457*    (2019.01)
    *G06F 16/9535*    (2019.01)
    *G16H 70/40*    (2018.01)

(52) U.S. Cl.
    CPC ....... *G16H 20/10* (2018.01); *G06F 16/24578* (2019.01); *G06F 16/9535* (2019.01); *G16H 70/40* (2018.01)

(58) Field of Classification Search
    CPC .... G16H 20/10; G16H 70/40; G06F 16/9535; G06F 16/24578
    See application file for complete search history.

(56) References Cited

U.S. PATENT DOCUMENTS

| 10,754,638 B1* | 8/2020 | Dwivedi | H04L 67/025 |
| 2010/0262556 A1* | 10/2010 | Shaya | G06Q 30/0641 705/347 |
| 2012/0005222 A1* | 1/2012 | Bhagwan | G06F 16/9554 707/769 |

(Continued)

FOREIGN PATENT DOCUMENTS

| WO | WO 2016/019353 A1 | 2/2016 | |
| WO | WO-2016019353 A1 * | 2/2016 | A24F 40/05 |

OTHER PUBLICATIONS

PCT International Search Report for International Application PCT/US2019/050067, search report dated Jun. 4, 2020 (Jun. 4, 2020).

*Primary Examiner* — Evangeline Barr
*Assistant Examiner* — Jordan L Jackson
(74) *Attorney, Agent, or Firm* — Daniel W. Roberts; Law Offices of Daniel W. Roberts, LLC

(57) ABSTRACT

Provided is a system and method for determining an appropriate dosage of a product. The method includes, receiving from a User a User Request for a Dosage, the User Request including at least a User Reason and a User Location; accessing a Database of Products, each Product having at least one Constituent, at least one Established Reason, a Dosage for each Established Reason, and Provider Location; querying the Database of Products with the User Request to determine at least a first subset of Products having the at least one Established Reason correlating to the User Reason; and providing the User with the first subset of Products arranged by proximity of the Provider Location to the User Location, the first subset of Products further including the Dosage for each Product in the first subset of Products. An associated system is also provided.

49 Claims, 9 Drawing Sheets

(56) References Cited

U.S. PATENT DOCUMENTS

| | | | |
|---|---|---|---|
| 2014/0236622 A1* | 8/2014 | Southam | G16H 20/30 |
| | | | 705/2 |
| 2015/0239645 A1* | 8/2015 | Eini | B01F 25/4232 |
| | | | 222/14 |
| 2016/0335543 A1 | 11/2016 | Goldstein et al. | |
| 2017/0266397 A1 | 9/2017 | Mayle et al. | |
| 2017/0304567 A1 | 10/2017 | Adelson | |
| 2018/0049999 A1* | 2/2018 | Quay | A61K 31/592 |
| 2018/0050164 A1 | 2/2018 | Adelson | |
| 2018/0052964 A1 | 2/2018 | Adelson | |
| 2018/0140787 A1* | 5/2018 | Hartman | A61M 15/008 |
| 2018/0369066 A1 | 12/2018 | Adelson | |
| 2018/0369514 A1 | 12/2018 | Adelson | |
| 2018/0370707 A1 | 12/2018 | Adelson | |
| 2019/0125968 A1* | 5/2019 | Kircher, Jr | G16H 50/50 |
| 2019/0289915 A1* | 9/2019 | Heidl | G06F 3/016 |
| 2020/0352249 A1* | 11/2020 | Achtien | A61M 15/0066 |
| 2021/0080441 A1* | 3/2021 | Bryant, Jr. | G16H 70/40 |

* cited by examiner

FIG. 2

CONSTITUENT LEVELS BY PRODUCT

| Product | ID | CBD | Careen | CBG | Pinene | CBC | Location | Delivery Modality |
|---|---|---|---|---|---|---|---|---|
| Product 1 March | 1142 | 81 | 7 | 7 | 23 | 1 | 123 Main; 420 East Green; | V, I |
| Product 1 June | 5928 | 80 | 7 | 29 | 6 | 3 | 955 Broadway | V, E |
| Product 2 | 2635 | 50 | 0 | 0 | 0 | 50 | 123 Main | V |
| Product 3 | 362 | 20 | 75 | 2 | 20 | 3 | 2424 S. Bart | V, E |
| Product 4 | 5232 | 0 | 5 | 1 | 14 | 80 | 904 Topaz; 1665 Coalton | V, S |
| Product 5 | 28088 | 25 | 5 | 20 | 30 | 20 | 420 East Green; 3915 S. Spruce | V |
| ... | | | | | | | | |
| Product N | 52172 | 82 | 3 | 3 | 20 | 75 | 955 Broadway; 420 East Green | V |

Established Reason

| Product | Anxiety | | | Pain | | | Insomnia | | | Glaucoma | | | Inflamation | | | Attention | | | Chronic Pain | | |
|---|---|---|---|---|---|---|---|---|---|---|---|---|---|---|---|---|---|---|---|---|---|
| | E | F | D | V | F | D | E | F | D | E | F | D | E | F | D | E | F | D | E | F | D |
| Product 1 March | 74 | 5 | 2 | 3 | 1 | 2 | 58 | 4 | 6 | 1 | 1 | 2 | 45 | 3 | 3 | 1 | 1 | 2 | 1 | 1 | 2 |
| Product 1 June | 73 | 3 | 2 | 8 | 1 | 2 | 20 | 2 | 4 | 1 | 1 | 2 | 1 | 1 | 2 | 72 | 5 | 4 | 1 | 1 | 2 |
| Product 2 | 30 | 1 | 4 | 0 | 1 | 2 | 0 | 0 | 0 | 72 | 5 | 3 | 65 | 4 | 6 | 1 | 1 | 2 | 1 | 1 | 2 |
| Product 3 | 1 | 0 | 0 | 21 | 3 | 2 | 68 | 5 | 5 | 1 | 1 | 2 | 1 | 1 | 2 | 1 | 1 | 2 | 1 | 1 | 2 |
| Product 4 | 1 | 0 | 0 | 45 | 4 | 2 | 1 | 1 | 2 | 1 | 1 | 2 | 1 | 1 | 2 | 1 | 1 | 2 | 78 | 5 | 4 |
| Product 5 | 20 | 2 | 3 | 65 | 5 | 2 | 30 | 5 | 5 | 1 | 1 | 2 | 1 | 1 | 2 | 1 | 1 | 2 | 1 | 1 | 2 |
| ... | | | | | | | | | | | | | | | | | | | | | |
| Product N | 74 | | 2 | 65 | | 2 | | | | | | | | | | | | | 78 | | 4 |

FIG. 3

CORRELATION TABLE

| Established Reason | Constituents | Products |
|---|---|---|
| Anxiety | CBD | Product 1 March (1142), Product 1 June (5928), ... |
| Pain | (CBG + Pinene + CDC) | Product 5 (52172), ... |
| Insomnia | Careen, (CBD+Pinene) | Product 3 (362), Product 1 March (1142), ... |
| Glaucoma | CDC | Product 2 (2635), ... |
| Inflammation | CBD | Product 1 March (1142), ... |
| Attention | CBG | Product 1 June (5928), ... |
| Chronic Pain | Pinene | Product 4 (5232), ... |

SYSTEM AND METHOD FOR DETERMINING AN APPROPRIATE DOSE OF A PRODUCT

FIELD OF THE INVENTION

The present invention relates generally to a system and method for providing a requesting party with an appropriate dosage for a product, its respective consistent makeup and dosage, in response to a specified reason. Such a reason may range from recreational to medicinal, and such dosage may be for a product to be vaporized, inhaled, eaten, topically applied, sublingually delivered or otherwise received by a body.

BACKGROUND

Plant based medicine products were very likely some of the earliest compounds that human beings used for the treatment of various ailments. Such recipes or formulae were often very general—a handful of moss, half a honey comb, three sprigs of lavender—and as such one person's remedy could be far more or less effective then another person's.

With advances in medicine and technology, there has come an awareness of chemical compositions and an enhanced appreciation and understanding of how for contemporary pharmaceuticals it is the precise measurement of one or more constituents that is responsible for properties of the pharmaceutical.

For example, although varying in brand name, traditional anti-itch creams typically have 1% hydrocortisone, anti-pain medications often have either 500 mg of acetaminophen or 200 mg of ibuprofen—these standard dosages of specific compounds are then combined with inactive ingredients for a variety of reasons, including taste, texture, delay of release, ease of dosing, stability, etc. . . . but fundamentally the ability of a person to rely on a product for a given reason is the certainty of consistency of the specific constituent that is known to address the reason for use—e.g., hydrocortisone for itching, ibuprofen for the treatment of pain or inflammation.

More recently, there has been a return to many plant based medicines and pharmaceuticals, as the natural plant materials have been found to provide medicinal benefits that may not be otherwise achieved through more traditional chemical composition development—i.e., laboratory based chemical compositions, or which are simply preferred by some people over traditional pharmaceutical medicine.

Whereas traditional pharmaceutical medicine is typically reliant upon one particular active ingredient, as noted above, contemporary plant based medicines are typically reliant on particular active ingredient constituent makeups and their relative ratios. However, these constituents may vary from crop to crop, and even from physical location to physical location.

Prior art platforms do exist and attempt to collect and report on various plant based medicinal preparations based on user feedback. However, significant shortcomings exist. Often, these systems or platforms are web based or mobile applications that track very superficial information, and are typically without significant context. Although these systems attempt to capture user preference feedback on what plant strains are more or less effective for a particular reason or ailment, they do not attempt to capture an understanding of the specific constituents, let alone acknowledge that these constituents may vary from one batch of a given product to the next.

Additional shortfalls occur as such systems are largely based on surveys of past use and not a quantification of use and experience on a session by session basis. Such surveys also typically have not attempted to track dosage amounts and how the dosage also correlates to the intended reason or ailment and the apparent experience of such use.

Laboratory analysis can be performed, and often is—where a sample of the refined or processed plant based material is tested and analyzed to identify the apparent constituents and level of their presence. In some instances, specific constituents may even be isolated and tested on cellular tissue, much as is the practice with more traditional pharmaceutical medicine. Although beneficial to a point, simple awareness of a constituent and level of presence is not necessarily meaningful regarding a relationship to a reason or ailment. In addition, if the values reported are for a product line, but not a specific batch, the values may be more of a general indicator of likely values and not actual values.

There is also a strong suspicion that multiple constituents may work together in concert to provide various beneficial effects. However due to the number of constituents and their varying levels from one crop or production batch to another, presently there is great ambiguity in determining and predictively assessing what combinations and ratios may be effective and which ones may be merely coincidental. In addition, "strains" and preparation "branding" are in some cases mere marketing labels and vastly different products may be marketed under the same or similar brand names—further adding to ambiguity in user perceptions and expectations.

Further, indication of a constituent and level of presence by itself may not be meaningful to a user attempting to select a plant based product for a specific reason or ailment without dosage information. Still further, different dosages of the same product may have different resultant affects for different reasons or ailments, and for different people.

Moreover, as constituent makeup varies widely there is a definite need to provide coordinated information regarding constituent makeup, constituent levels, coordination of constituent(s) to reasons or ailments, dosage and user feedback to specific batch products of plant based medicinal remedies.

Hence there is a need for a method and system that is capable of overcoming one or more of the above identified challenges.

SUMMARY OF THE INVENTION

Our invention solves the problems of the prior art by providing novel systems and methods to determine an appropriate dose of a product and solves various problems with the existing state of the art methods.

In particular, and by way of example only, according to at least one embodiment, provided is a method of determining an appropriate dose of a product, including: receiving from a User a User Request for a Dosage, the User Request including at least a User Reason and a User Location; accessing a Database of Products, each Product having at least one Constituent, at least one Established Reason, a Dosage for each Established Reason, and Provider Location; querying the Database of Products with the User Request to determine at least a first subset of Products having the at least one Established Reason correlating to the User Reason; and providing the User with the first subset of Products arranged by proximity of the Provider Location to the User Location, the first subset of Products further including the Dosage for each Product in the first subset of Products.

In yet another embodiment, provided is a method of determining an appropriate dose of a product, including: using a first instance of an application on a first user computing device for receiving from a User a User Request for a Dosage, the User Request including at least a User Reason and a User Location, the first instance of the application accessing a remote first server system having a processor and a Database of Products, each Product having at least one Constituent, at least one Established Reason, a Dosage for each Established Reason, and Provider Location, the Database of Products further having a Correlation Table correlating Established Reasons to Constituents; querying the Database of Products with the User Request to determine at least a first subset of Products having the at least one Established Reason correlating to the User Reason; providing the first user computing device with the first subset of Products arranged by proximity of the Provider Location to the User Location, the first subset of Products further including the Dosage for each Product in the first subset of Products.

And for yet another embodiment, provided is a system for determining an appropriate dose of a product, including: a remote server system having a processor and a Database of Products, each Product having at least one Constituent, at least one Established Reason, a Dosage for each Established Reason, and Provider Location, the Database of Products further having a Correlation Table correlating Established Reasons to Constituents; and at least one remote Application for determining an appropriate dose of a product for installation upon a remote computing device having a processor and a location element, the remote application communicating with the remote server to provide a User Request for a Dosage, the User Request including at least a User Reason and a User Location; wherein in response to the User Request, the remote server: queries the Database of Products with the User Request to determine at least a first subset of Products having the at least one Established Reason correlating to the User Reason, and provide the remote application with the first subset of Products arranged by proximity of the Provider Location to the User Location, the first subset of Products further including the Dosage for each Product in the first subset of Products.

BRIEF DESCRIPTION OF THE DRAWINGS AND SUPPORTING MATERIALS

FIG. 2 illustrates a table for the Database of Products in accordance with at least one embodiment;

FIG. 3 illustrates a correlation table for the products, constituents and established reasons in accordance with at least one embodiment;

DETAILED DESCRIPTION

Figure 1:
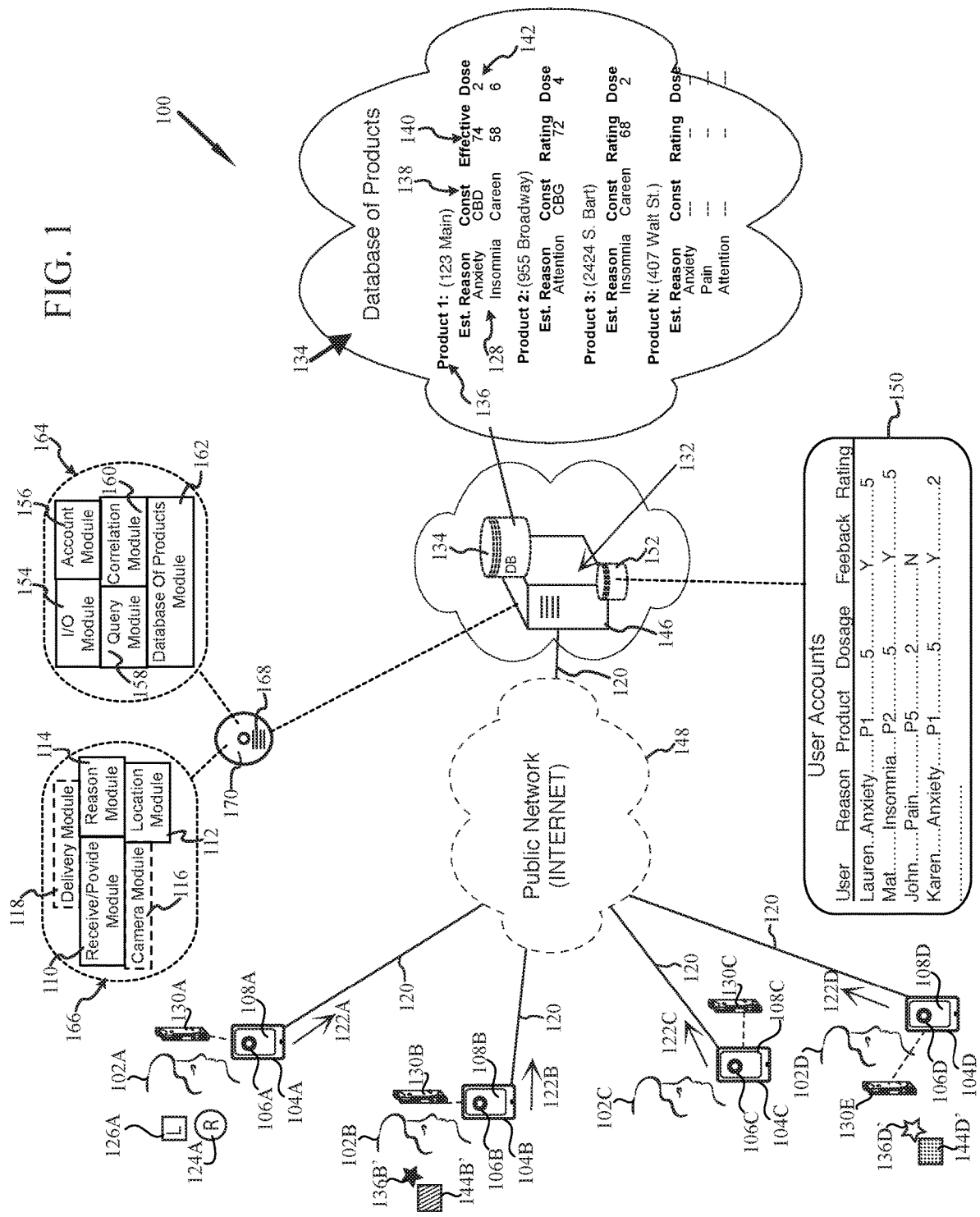
FIG. 1 illustrates a high level diagram of a system for determining an appropriate dose of a product in accordance with at least one embodiment.

Before proceeding with the detailed description, it is to be appreciated that the present teaching is by way of example only, not by limitation. The concepts herein are not limited to use or application with a specific system or method for determining an appropriate dosage of a product. Thus, although the instrumentalities described herein are for the convenience of explanation shown and described with respect to exemplary embodiments, it will be understood and appreciated that the principles herein may be applied equally in other types of systems and methods for determining dosage of a product.

This invention is described with respect to preferred embodiments in the following description with reference to the Figures, in which like numbers represent the same or similar elements. Further, with the respect to the numbering of the same or similar elements, it will be appreciated that the leading values identify the Figure in which the element is first identified and described, e.g., element 100 first appears in FIG. 1.

Various embodiments presented herein are descriptive of apparatus, systems, articles of manufacturer, or the like for systems and methods involving determining an appropriate dose of a product. In some embodiments, an interface, application browser, window or the like may be provided that allows the user of the computing device to direct behavior of the computing device.

Moreover, some portions of the detailed description that follows are presented in terms of the manipulation and processing of data bits within a computer memory. The steps involved with such manipulation are those requiring the manipulation of physical quantities. Generally, though not necessarily, these quantities take the form of electrical or magnetic signals capable of being stored, transferred, combined, compared and otherwise manipulated. Those skilled in the art will appreciate that these signals are commonly referred to as bits, values, element numbers or other clearly identifiable components.

It is of course understood and appreciated that all of these terms are associated with appropriate physical quantities and are merely convenient labels applied to these physical quantities. Moreover, it is appreciated that throughout the following description, the use of terms such as "processing" or "evaluating" or "receiving" or "outputting" or the like, refer to the action and processor of a computer system or similar electronic computing device that manipulates and transforms the data represented as physical (electrical) quantities within the computer system's memories into other data similarly represented as physical quantities within the computer system's memories.

The present invention also relates to an apparatus for performing the operations herein described. This apparatus may be specifically constructed for the required purposes as are further described below, or the apparatus may be a general purpose computer selectively adapted or reconfigured by one or more computer programs stored in the computer upon computer readable storage medium suitable for storing electronic instructions.

To further assist in the following description, the following defined terms are provided.

"User"—typically a person or at the very least a computing device used by a person who is known to the dosing system, or an administration system that is in communication with the dosing system in the sense that the he or she has established a User account by providing a threshold of data, e.g. attributes, to identify themselves. Typically it is expected that the Users' interactions with the dosing system or the related administration system will also serve to establish additional Attributes about themselves.

"First Device"—the computing device having at least one processor that is used by the person/User desiring a dosage of a Product for a specified User Reason.

"Reason"—the purpose or ailment for which a User is requesting a dosage, such as but not limited to: acute pain, anxiety, arthritis, cancer, chronic pain, focused attention, glaucoma, inflammation, insomnia, multiple sclerosis (MS), general pain or muscle soreness, relaxation, stress, sleepiness, and treatment of tremors. When the User is providing the Reason, this is understood and appreciate to be a User Reason as it is the intended purpose for which the dosage is requested. Within the Dosing System, Established Reasons are records correlating prior user dosages and reported experiences to constituent(s) of Products.

"Dosing System"—The system to which Users connect when requesting a dose/dosage of a Product or a Reason. The Dosing System maintains or at least interacts with a Database of Products.

"Database of Products"—an indexed set of records correlation Products, one or more Constituents for each product, Established Reasons for which Products have been used, dosages associated to Reasons, and User evaluation feedback. The Database of Products may be established as a relational database and may be localized upon one or more computing systems in a specific location, or distributed such as in a cloud computing space.

"Product"—a compound that may be provided as a liquid, liquid concentrate, edible medium, inhalant, tablet, semisolid, cream, or other form that may be consumed by a physical person. Generally, this is understood and appreciated to be a plant based medicinal compound. However, it is understood and appreciated that in varying embodiments, a Product or Products may also be a pharmaceutical, organic, and/or synthetically derived compound. Further still, for yet another embayment, a Product may be provided as a combination of elements selected from the group consisting of, plant, animal, mineral, organic, pharmaceutical, and synthetic compounds.

"Constituent"—an identifiable element of a plant based product, such as, but not limited to a cannabinoid and or a terpene, and various specific forms thereof including, but not limited to cannabinoid selected from THC, THC-A, CBN, CBG, CBC, CBD, CBD-A, THCV, and CBDV, and terpene selected from Alpha-Ocimene, Beta-Ocimene, Camphene, Careen, Caryophyllene, Carophyllene oxide, Cymene, Eucalyptol, Isopulefgol, Limonene, Linalool, Myrcene, Pinene, Terpinine, Terpinolene. Moreover, for at least *cannabis* plant products there are known to be more than 400 different chemical compounds with more than 60 identified as cannabinoid compounds. In varying embodiments, Constituents may also be non-*cannabis* elements, such as but not limited to psilocybin.

"Correlation Table"—an index of Constituents and their effectiveness in addressing Reasons. More specifically, although a correlation may be determined between a given Constituent and a given Reason, through the aggregation of data in the Database of Products, correlations between multiple Constituents in concert with each other are correlated to a given Reason. In varying embodiments, the Correlation Table permits not only the identification of which Products provide one or more Constituent(s) most suitable for a given Reason, but may advantageously direct the development of new Products, combinations of Products, and/or refinement of Products having the most desirable Constituent combination for a given Reason.

"Modality of Delivery"—the method of delivery for the product, selected to correspond with the type and nature of the product, and generally understood to be selected from the group consisting of vaporization, inhalation, edible, sublingual, topical, buccal, suppository, and ophthalmic.

"Attribute"—an element of data that is distinct to the Product, such as a bar code, QR code, listing of actual constituents and levels, or other data, the Attribute permitting specific identification of one or more constituent and apparent level of the one or more consistent for a specific product.

With respect to the above defined terms, it is understood and appreciated that for at least one embodiment, each module or system is implemented as a collection of independent electronic circuits packaged as a unit upon a printed circuit board or as a chip attached to a circuit board or other element of a computer so as to provide a basic function within a computer. In varying embodiments, one or more modules may also be implemented as software that adapts a computer to perform a specific task or basic function as part of a greater whole. Further still, in yet other embodiments one or more modules may be provided by a mix of both software and independent electronic circuits.

To briefly summarize, provided is a system and method for determining an appropriate dose of a Product. In general, a User has a smartphone or other portable computing device that has been configured with Internet access and adapted by specific software instructions to perform the specific features and benefits for communicating with a Dosing System in accordance with at least one embodiment of the present invention. More specifically, for at least one embodiment, the User has an Application installed upon his or her portable computing device, the Application permitting the User to connect with the Dosing System.

The Application further permits the User to specify at least one User Request for a Dose of a Product. The User Request includes at least a User Reason and a user location. The user Location may be determined by GPS or by user specific designation. The Dosing System receives the User Request and accesses a Database of Products, each Product having at least one Constituent and at least one Established Reason and dose for that Established Reason, and a provider location. The Dosing System queries the Database with the User request to determine at least a first subset of Products having an Established Reason correlating to the User Reason. The Dosing System returns at least a portion of the first subset of Products arranged by the proximity of the provider location to the User location.

This summary may be more fully appreciated with respect to the following description and accompanying figures.

Turning now to the drawings, and more specifically, FIG. 1, there is shown a high level diagram of an embodiment of the System for Determining Appropriate Dose of a Product, e.g., SDADP 100, for Users 102 having First Devices 104. For at least one embodiment, interaction with SDADP 100 by the Users 102 is further facilitated by the First Devices 104 having an App 106 which adapts the First Device 104 for interaction with the remote elements of SDADP 100. For at least one alternative embodiment, SDADP 100 may optionally permit Users 102 to connect via a web browser in place of the Application 106.

With respect to FIG. 1, for the present example there are shown a plurality of Users 102, of which Users 102A, 102B, 102C and 102D are exemplary. Each user 102A-102D has a corresponding First Device 104, of which First Devices 104A-104D are exemplary, each understood and appreciated to be a computing device having at least one processor. Further, each First Device 104A-104D has an instance of a Dosing App, or "DA" 106 and a visual display screen 108, e.g. display screens 108A-108D.

As will be more fully appreciated below, each active instance of DA 106 adapts the First Device 104 by providing a receive/provide module 110, a determine location module 112, a specify Reason module 114. For at least one embodiment, the DA 106 also provides an optional camera interface module 116. Further, for yet another embodiment, the DA 106 also provides an optional delivery module 118.

Each first device 104A-104D is also enabled for network communication 120, such as by wireless network communication. Further still, each First Device 104 also has a location determining ability, such as GPS. The Users 102 location may thus be determined and included with the User Request 122 when poised to SDADP 100. For at least one embodiment, each User Request 122 includes a User Reason 124 and the User location 126, shown in detail for User 102A, but omitted for Users 102B, 102C and 102D. Additional information may also be included, such as time and date, User ID or account info, etc. . . .

For the present example, each First Device 104 has been illustrated as a wireless smart phone, but may alternatively comprise a portable computer or data assistant device that is capable of portable wireless communication using WiFi networks, wireless network access points, cellular networks, GPS transmissions, and or other such technologies. Moreover, for at least one embodiment, the First Devices 104A-104D are smart phone devices such as, but not limited to the Apple Computers iPhone® or Samsung Android® device.

Moreover, SDADP 100 permits Users 102 with First Devices 104 having an instance of the dosing application "DA" 106 to request and receive a specific dose for a Product which has been correlated to their indicated User Reason 124—i.e., anxiety, pain, attention, sleeplessness, etc. . . . As is further detailed below, it is specifically understood and appreciated that SDADP 100 advantageously acts to correlate a specified User Reason 124 to an established and live database that permits SDADP 100 to identify one or more Products having one or more Constituents that correlate to Established Reasons 128 which in turn are evaluated to the User Reason 124. With such a Product identified, SDADP 100 then provides the requesting User with the identity of the Product, the dosage for the product, and the location of a product provider from which the product may be obtained.

As is also shown in FIG. 1, each User 102 has a dosage device 130, of which dosage devices 130A-130E are exemplary, that is structured and arranged to receive a removable reservoir of a Product and to provide the dosage of the Product that is determined appropriate for the Reason 124 specified by the User 102. Moreover, for at least one embodiment, the dosage device 130 is an operable device in wireless communication with the User's first device 104 such that dosing information for a product is provided to the dosage device 130 by the first device 104. More specifically, for at least one embodiment, dosage device 130 is a smart device, having at least one processor with associated memory, control instructions, and optionally at least one detector such that dosage device 130 is advantageously operable to detect the type of Product in a removable reservoir when coupled to the dosage device 130, and provide a metered dosage of the Product appropriate for the Reason 124 specified by the User 102.

In varying embodiments, the dosage device 130 may be a vaporizing device structured and arranged to receive a reservoir of Product in the form of a concentrate cartridge. More specifically, for at least one embodiment, the dosage device 130 is a vaporizing device as disclosed in U.S. application Ser. No. 15/177,325 entitled Portable Vaporizer for Dosing Concentrate Material, now U.S. Pat. No. 10,426,196 incorporated herein by reference. For yet another embodiment, the dosage device 130 is a vaporizing device as disclosed in U.S. application Ser. No. 15/391,929 entitled System and Method for Managing Concentrate Usage, now U.S. Pat. No. 10,834,967 incorporated herein by reference. And for yet another embodiment, the dosage device 130 is a vaporizer as disclosed in PCT application PCT/US19/28541 and entitled Improved Vaporizer System and Method for Managing Concentrate Usage, incorporated herein by reference. And yet further still, for another embodiment, the dosage device 130 is a dosing device as disclosed in U.S. Provisional Application 62/787,650 and entitled Dosing Device and System, incorporated herein by reference.

For at least one alternative embodiment, dosage device 130 is structured and arranged to accept a plurality of different reservoirs of Products, at least two different Products having different modalities of delivery. Moreover, for at least one embodiment dosage device 130 can receive in a first instance a first reservoir of Product in the form of a first cartridge of Product that is intended administration to the user by vaporization, and in a second instance a second reservoir of Product in the form of a second cartridge of Product that is intended for administration to the user 102 as sublingual powder or fluid, and in a third instance a third reservoir of Product in the form of a third cartridge of Product that is intended for edible administration to the user 102. Of course, in varying embodiments dosage device 130 may provide a User 102 with other optional modalities of delivery, or be specifically tailored to one or two modalities of delivery.

Moreover, dosage device 130 is understood and appreciated to be a metering dosage device structured and arranged to provide a specified dosage of a Product. In varying embodiments, the dosage device 130 may be configured to provide a Product for a specific modality of delivery, or provide a dosage applicable to at least two different modalities of delivery. For at least one embodiment, the User 102 sets the dosage device 130 for the prescribed dosage indicated by SDADP 100.

As dosage device 130 is in wireless communication with the First Device 104, the dosage device can report the dosage administered back to SDADP 100. For at least one alternative device, the dosage level may be communicated from SDADP 100 to the dosage device 130 directly or by way of the first device 104, and the dosage device 130 may automatically configure for the prescribed dosage upon confirming that a proper reservoir of the correlated Product is coupled to the dosage device 130.

In addition to the DA 106 provided to the First Devices 104, SDADP 100 includes a Dosing System 132 in data communication with a Database of Products 134. Dosing system 132 is understood and appreciated to be a remote first server system—e.g. a computing system distinct from the First Devices 104 of the Users 102, or other User 102 devices.

As noted above, and shown conceptually in FIG. 1, the Database of Products 134 provides a record of Products 136 known to SDADP 100. For at least one embodiment of the present invention, for each Product 136 recorded to the Database of Products 134, there is at least one associated Constituents 138, an Established Reason 128, a rating of effectiveness 140 and a dosage 142.

A more detailed example of the Database of Products 134 is presented in FIG. 2 as discussed below. Moreover, it is an advantageous aspect of the present invention that SDADP 100 correlates Established Reasons 128 to one or more constituents 138 of Products 136 so as to establish a searchable index to identify which Products 136 are most desirable for treating a specified reason that is matched to an Established Reason 128.

For at least one embodiment, manufacturers, growers, or other providers of Products 136 perform analysis upon each batch of their Products 136 to determine the present levels of at least some constituents. Each such tested Products 136 may be coded with an Attribute 144—such as a bar code, QR Code, or other indicia, including a human readable listing of at least some constituents and their determined levels. Accordingly, each Attribute 144 marked Product 136 can be uniquely identified, tracked and analyzed within the Database of Products 134. With respect to FIG. 1, user Products 136B' and 136D' are shown to have corresponding Attributes 144B' and 144D'.

With respect to FIG. 1, User 102B has a user Product 136B' represented by a solid star, and this user Product 136B' has unique attribute 144B'. Similarly, User 102C is shown to have a user Product 136C' that is represented by an outline star, and this user Product 136C' has a unique attribute 144C'. Moreover, it will be understood and appreciated that these two exemplary user products 134' and their associated attributes 144' are different.

Each Product 136 may have hundreds of Constituents 138, however for at least one embodiment of the present invention, only a subset of constituents is noted and present—more specifically, those Constituents 138 that have been correlated to one or more Established Reasons 128 are noted in the database of Products 134. The rating of Effectiveness 140, or more specifically the rating values identifying the degree of likely effectiveness are in essence an evaluation of a given Product 136 in terms of effectiveness for an Established Reason 128. The rating of Effectiveness 140 may be initialized by a pre-existing understanding of a Constituent 138 correlating to an Established Reason 128, but for at least one embodiment, the rating of Effectiveness 140 is further adjusted in response to User 102 feedback provided to SDADP 100 at one or more time periods following SDADP 100 determining a dose for a User Reason 124.

More simply stated, because plant based Products 136 may vary from crop to crop as well as from processed batch to processed batch, it is entirely possible, if not even likely, that different batches of the same Product 136 may have different constituent levels and different performance characteristics with respect to Established Reasons 128. SDADP 100 therefore polls Users 102 following the delivery of a dosage, Product 136, and the identification of a product provider, or confirmation that a User Product 136' is acceptable, to inquire from the User 102 how the prescribed dosage of the Product 136 is meeting the expectations of the User 102 in satisfying the User Reason 124.

For at least one embodiment, the first device 104 is in wireless communication with a delivery device, such as a vaporizer, so that SDADP 100 is provided with confirmation of the time, dosage and Product 136 used by the User 102. The timing of follow-up for User Feedback by SDADP 100 is then performed in a highly relevant time frame and able to receive contemporaneous evaluation as feedback rather than a historical recollection. In such a way, Product A may be identified to be better for a User Reason 124 identified as anxiety then Product A'—marketed under the same name but with slightly different constituent makeup.

It is to be understood and appreciated that the Dosing System 132 is a remote system, meaning that it is physically distinct from the First Devices 104. Similarly, the Database of Products 134, whether a component of the Dosing System 132 or another system in communication with the Dosing System 132 is distinct and separate from the First Devices 104.

Moreover, the Dosing System 132 is provided by at least one physical computer system 146 (including at least one microprocessor, memory, I/O device(s) and the like) that is adapted by hardware or software to provide Dosing System 132. For an embodiment where the Database of Products 134 is a separate system from the Dosing System 132, the Database of Products 134 is also understood and appreciated to be provided by at least one physical computer system (including at least one microprocessor, memory, I/O device(s) and the like) that is adapted by hardware or software to provide Database of Products 134.

In varying embodiments, one or more of the elements of SDADP 100 may be directly connected to one another, if not integrated with each other, but it is understood and appreciated that in most instances the incorporation of the Internet 148 as a common means of communication and information exchange is within the scope of the present invention.

It is also to be understood and appreciated that the elements of the SDADP 100 need not maintain continual communication links 120—be them physical wire or wireless links. In other words, Users 102 may log on or off, and thus establish a link to Dosing System 132. Likewise, the Dosing System 132, the Database of Products 134, and such other network systems and/or devices may be in intermittent connection—connecting when and as necessary for the intended operation of SDADP 100.

For at least one embodiment, the Dosing System 132 also has a record 150 of details for each user account. In varying embodiments, this record 150 may be a component integrated with the Dosing System 132, or a remote database to which the Dosing System 132 has access rights when and as needed. For the present example as shown, the database 152 supporting record 150 is shown as a component of the Dosing System 132.

As conceptually shown, for at least one embodiment, for each User 102 of SDADP 100, the account record 150 notes user name/ID, at least the last Reason, at least the last product and dosage determined, whether feedback has been received, and what that feedback was.

For at least one embodiment, the Dosing System 132 is provided by hardware and/or software adapting the physical system 146 to provide an I/O module 154, an account module 156, a query module 158, a correlation module 160 and a database of products module 162. Moreover, for at least one embodiment, and with respect to FIG. 1, SDADP 100 may be further appreciated to be a client & server type of computer system. More specifically, the server component 164 is provided by the I/O module 154, the account module 156, the database of products module 162, the correlation module 160, and the query module 158. The client component 166, aka DA 106, is provided by the receive/provide module 110, the location module 112, the specify Reason module 114, the optional camera module 116, and the optional delivery modality module, e.g. delivery module 118.

With respect to the client, e.g. DA 106, the receive/provide module 110 is structured and arranged to permit a user to receive and provide data to SDADP 100 at a general level—to set up a user account and subsequently log in and to select among a variety of options such as a review of the Users history of use, to initiate a new User Request 122, to initiate a mapping application for directions to a provider location, and to initiate use of the First Device camera, among other possible actions.

The receive/provide module 110 is effectively an I/O module, but it has been identified by a different label herein so as to avoid possible confusion with the I/O module of the Dosing System 132/Server component 164. The receive/provide module 110 may also be remotely triggered by the Dosing System 132 so as to follow-up with the User 102 regarding the effectiveness of a determined dose with respect to the User Reason 124 at one or more time intervals following the delivery of the dose, Product identity and Provider location.

The location module 112 is typically a background application utilizing the location determining abilities of the First Device 104 to note the location of the User. For at least one embodiment, the User 102 has the ability to over-ride this automatic determination so as, for example, to set a future location—i.e., home, work or other known remote location, where the User 102 intends to be as a preferred location around which to identify provider locations.

The specify Reason module 114 permits the User 102 to specify at least one Reason for which they are desiring a dosage. Moreover, for at least one embodiment of the present invention, it is to be understood and appreciated that the User 102 is using SDADP 100 to determine a dosage that is appropriate to address his or her Reason—the User Reason 124. SDADP 100 advantageously establishes and revises the Database of Products 134 so as to correlate Established Reasons 128 to Products 136, thus permitting the User Reason to be evaluated and matched to Established Reasons so as to identify at least a subset of Products 136 appropriate for the User Reason 124.

In other words, different Products 136 are appropriate for different Established Reasons 128, and it is an aspect of the present invention of SDADP 100 to identify the best Product 136 for the User's specified User Reason 124.

The Reason—Established Reason 128 or User Reason 124—may be, but is not limited to, acute pain, anxiety, arthritis, cancer, chronic pain, focused attention, glaucoma, inflammation, insomnia, multiple sclerosis (MS), general pain or muscle stiffness, relaxation, stress, sleepiness, and treatment of tremors. For at least one embodiment, the User Reason 124 is selected from a drop down or scrolled list of pre-populated reasons so as to focus the User 102 to select from Reasons that are known to SDADP 100, though it will be understood and appreciated that this list may undergo continual update and revision.

For at least one embodiment, the User 102 may be permitted to specify a User Reason 124 through a text box—natural language heuristics being employed in an effort to identify and correlate the user provided statement to one or more Established Reasons 128. For at least one embodiment, if an automated process cannot match the User Reason 124 to an Established Reason 128, a human operator may be engaged to review and suggest an Established Reason 128.

Further, for at least one embodiment, the Reason module 114 may further permit the User 102 to specify a preferred modality of delivery for the Product(s) 136 determined by SDADP 100 to be correlated to the User Reason 124, or an optional delivery module 118 module may be provided. Such optional modalities of delivery may be selected from, but not limited to, vaporization, inhalation, edible, sublingual, topical, buccal, suppository, and ophthalmic. Of course, in varying embodiments, a different or additional module may be present the User 102 with the option to specify a preferred modality of delivery. Moreover, for at least one embodiment, SDADP 100 advantageously permits users to request preferred options for delivery. As such, a User having reduced breathing capacity may request a sublingual or edible Product option over a vaporized or inhalant Product.

The camera module 116 permits the User to use the camera of the First Device 104 to acquire an Attribute 144 from Product 136 that the User 102 has at hand—i.e., User 102B having a User Product 136' obtains Attribute 144B'. More specifically, the camera module 116 permits the User 102 to scan a bar code, UPC code, QR code, or other readable code or data so that SDADP 100 may uniquely identify the User Product 136'.

As noted above, a User may have a dosage device 130, and for at least one embodiment, the user's dosage device 130 may be structured and arranged to receive the unique Attribute 144 from a Product 136 that is disposed at least partially within the dosage device 130. For example, in certain embodiments the product attribute 144 may be provided a smart chip that is disposed within the housing of the product and pre-positioned so as to be readable by reader within the dosage device 130. When such a smart chip on the Product 136 and reader within the dosing device 130 are present, the Attribute 144 may be communicated from the dosage device 130 to the First Device 104, and more specifically the DA 106, for communication back to SDADP 100, as an optional alternative to the User 104 making use of the camera module 116. While such an option may be advantageous for the User, it is specifically understood and appreciated that communication between the dosage device 130 and the First Device 140, specifically the DA 106, is not required for implementation of embodiments of the present invention.

For at least one embodiment, when this Attribute 144 is provided by the DA 106 to the Dosing System 132, this unique Attribute 144 is compared to the Products 136 in the Database of Products 134 to determine if a match exists. If a match is found then the SDADP 100 will have an established record correlating the User Product 136' to one or more Established Reasons 128 and SDADP 100 can determine if the User Product 136' is appropriate for the User Reason 124, or if a more beneficial Product 136 should be prescribed.

Where the unique Attribute 144 does not match to a Product 136 within the Database of Products 134, for at least one embodiment, the unique Attribute 144 may contain information as to the manufacturer, and SDADP 100 can initiate a request for information regarding the constituents 138 of the User Product 136'. For yet another embodiment, if the Attribute 144 does not match to a Product 136 within the Database of Products 134, and/or SDADP 100 is unable to receive constituent information directly from the manufacture, SDADP 100 may optionally invite the User 102 to provide constituent information as provided on the User Product 136'. Such constituent information may be provided by optical character recognition of a photo of such information as provided by the User 102, or by permitting the User 102 to type in, or speak each indicated constituent and its reported level within the User Product 136'.

With respect to the server component 164, the I/O module 154 is structured and arranged to receive data from the First Device 104, such as, but not limited to account setup requests, account log in and log out actions, User Requests 122 (including a User Reason 124 and Location 126), and User feedback. The I/O module 154 is further structured and arranged to direct data to the First Device 104, such as a determined dosage and Product 136, a Product provider location, a request for User feedback, and/or such other information as may be desired and helpful to the User 102 and operation of SDADP 100.

The account module 156 is structured and arranged to permit the User 102 to initialize his or her account with his or her remote First Device 104, and subsequently to update his or her account details including, but not limited to, location, mood, heath state, Products used, dosages used, rating of effectiveness, User Products presently in inventory, and the like.

The database of products module 162 is a core element of the present invention. The database of products module 162 establishes and maintains the Database of Products 134, wherein distinct Products 136 are identified with one or more Constituents 138, the correlation of the Constituents 138 to one or more Established Reasons 128, the User feedback regarding the correlations, and the physical locations of known providers of the Products 136. More specifically, as Products 136 may vary from production batch to production batch, geographic location, and other factors, the present invention advantageously seeks to track and identify distinct production batches of Products 136. As such, the unique characteristics and correlations to Established Reasons 128 can be identified and used to subsequently identify Products 136 that correlate strongly to User Reasons 124.

The correlation module 160 is, for at least one embodiment, structured and arranged as an autonomous module operating in one embodiment at specific time intervals if not continuously cycling through the Database of Products 134. In simple terms, the correlation module evaluates the user feedback regarding how effectively the dosage met the User Reason 124 so as to provide an improved correlation score value to an Established Reason 128. For at least one embodiment, multiple Constituents 138 may be correlated to each Established Reason 128. Further still, for at least one embodiment the correlation module 160 develops at least one first Correlation Table correlating Established Reasons 128 to Products 136 that have been determined to be highly applicable. In addition, correlation module 160 may further develop at least one second Correlation Table correlating Established Reasons 128 to one or more Constituents 138.

More specifically, at least one embodiment of SDADP 100 advantageously leverages use by a plurality of Users 102 and the aggregation of data to develop correlations between the vast numbers of constituents that may be present in a Product 134. Indeed, Users 102 provide real time data to SDADP 100 and for at least one embodiment the correlation module 160 operates to identify and develop correlations between Constituents 138 and Establishes Reasons 128 in real time as well. With a large number of users expands, SDADP 100 is advantageously able to determine correlations at a rate and precision not previously available.

Indeed, the aggregation of data made available to SDADP 100 will permit a variation of SDADP 100 to provide growers, producers and manufacturers with meaningful data regarding which Constituents 138, and more importantly which combinations of Constituents 138, are most desirable for addressing Established Reason 128. Indeed, for at least one embodiment of SDADP 100 the correlation module 160 and the Correlation Tables may advantageously be adapted for the development of new Products from the combination of existing products, or specific growing and processing efforts to derive a new Product with a plurality of ccs operating in concert to address an Established Reason 128 more effectively than can be achieved with presently known Products.

Returning to the present examples and exemplary Correlation Tables, those skilled in the art will appreciate that these first and or second Correlation Tables advantageously permit SDADP 100 to quickly identify which Products 136 are suitable for a specified User Reason 124, and more advantageously, to predict which Products 136 may be suitable for a specified User Reason 124, based on a correlation of the Constituents 138 of a Product that is new or generally unknown to Products with similar constituents 138 and established correlations to Established Reasons 128.

It is further to be understood and appreciated that a Constituent 138 that is effective for a first Established Reason 128 may not be so for a second Established Reason 128. Further, different dosages may also adjust the correlation—i.e., a first dosage may be appropriate for a first Established Reason 128, but a second dosage (different from the first) may be appropriate for a second Established Reason 128 that is distinct and different from the first Established Reason 128. In other words, the same Product 136 administered at different dosages may be appropriate for different Established Reasons 128.

The query module 158 is structured and arranged to query the Database of Products 134 with the User Reason 124 for comparison to Established Reasons 128 so as to identity at least a first subset of Products having at least one Established Reason 128 correlation to the User Reason 124. In other words, the query function searches the Database of Products 134 to identify Products that appear to satisfy the User Reason 124 (e.g., chronic pain for a first user and insomnia for a second user). It is to be fully understood, appreciated and expected that different Products and even different dosages of the same Product may have diffident correlations to Established Reasons 128. The query module will also retrieve the location of known Providers for correlated products in the first subset.

For embodiments of SDADP 100 wherein the user 102 provides an Attribute 144 of a User Product 136', the query module 158 may further compare the User Product 136' to known Products 136 in the Database of Products 134 so as to determine if the User Product 136' is a suitable Product 136 for the User Reason 124. Such a comparison to known products may be achieved by matching the User Product 136' to a known Product 136 in a first instance, or in a second instance, matching the constituent levels indicated by the Attribute 144 to constituent levels of Products 136 that correlate to the User Reason 124.

With respect to FIG. 1, the elements of client component 166, aka DA 106 (the receive/provide module 110, the location module 112, the specify Reason module 114 and the camera module 116), and the server component 164, aka Dosing System 132 (the I/O module 154, the account module 156, the database of products module 162, the correlation module 160, and the query module 158), are conceptually illustrated in the context of an embodiment for at least one computer program 168. Such a computer program 168 may be provided upon a non-transitory computer readable media, such as an optical disc 170 or USB drive (not shown), having encoded thereto an embodiment of a program for SDADP 100.

Moreover, the computer executable instructions for computer program 168 regarding the server component 164, aka Dosing System 132 are provided to the computer system 146. During operation of SDADP 100, the computer executable instructions may be maintained in active memory for enhanced speed and efficiency.

For at least one embodiment the client component 166, aka the modules comprising DA 106 may be provided directly to desiring Users 102 by the remote Dosing System 132. For at least one alternative embodiment, the modules comprising DA 106 are made available from a third party such as, but not limited to the Apple® App Store, or Google® Play, or such other third party application provider. And for yet another embodiment, the modules comprising DA 106 may be separately provided on a non-transitory computer readable media for upload to such a third party application provider or even to User 102 directly for direct installation upon his or her first device 104.

To summarize, for at least one embodiment, the present invention provides a system for determining an appropriate dose 142 of a Product 136, including: a remote server system having a processor and a Database of Products 134, each Product 136 having at least one Constituent, at least one Established Reason 128, a Dosage 142 for each Established Reason 128, and Provider Location, the Database of Products 134 further having a Correlation Table 300 (see FIG. 3 below) correlating Established Reasons 128 to Constituents 138; at least one remote Application for determining an appropriate dose of a Product 136 for installation upon a remote computing device having a processor and a location element, the remote application communicating with the remote server to provide a User Request 122 for a Dosage 142, the User Request 122 including at least a User Reason 124 and a User Location 126; wherein in response to the User Request 122, the remote server: queries the Database of Products 134 with the User Request 122 to determine at least a first subset of Products having the at least one Established Reason 128 correlating to the User Reason 124, and provide the remote application with the first subset of Products 136 arranged by proximity of the Provider Location to the User 102 Location, the first subset of Products 136 further including the Dosage 142 for each Product 136 in the first subset of Products 136.

FIG. 2 provides a more detailed conceptual view or the Database of Products 134. The organization of this Database of Products 134 may take many forms, including, but not limited to a relational database, distributed or flat file. For at least one embodiment, as well as ease of illustration, Database of Products 134 is represented at least in part as a table 200, shown in two parts—part 200A for Products 136 and their respective Constituents 138, and part 200B for Products 136 and their relationship to a subset of Established Reasons 128. With respect to parts 200A and 200B, it is to be understood and appreciated that the identified constituents 138 and Established Reasons 128 are essentially fictitious with respect to the Products 136 shown. Moreover, while actual constituent titles and established reason titles have been used, this application does not intend to suggest or imply a true correlation between the constituents and reasons as shown—these relationships have been shown for the ease of illustration and discussion, and as the relationships and correlations are understood to be evolving, these illustrated relationships have been established for discussion purposes only.

As shown, table 200A presents a series of entries, and for the present example, seven (7) different Products 136—specifically Products 202A-202G, although Product 1 is shown in two types—Product 1 March 202A and Product 1 June 202B. As previously noted, with plant based products it is not uncommon for there to be variations in constituent make up from harvest to harvest and/or production batch to production batch. As such, with respect to the Database of Products 134, each distinct batch of a product is treated as a unique Product 136. Moreover, for at least one embodiment, each Product 136/202 present in the Database of Products 134 has a unique ID 204. For at least one embodiment, the unique ID 204 is at least a portion of the unique Attribute 144 of a Product 136/202. For yet another embodiment, the unique Attribute 144, or portion thereof, is recorded in an additional field not shown in the present example of table 200.

As shown for the present example, each Product 202 also has a listing of at least a subset of constituents 206, and for at least one embodiment these are selected based on an understanding and belief that these constituents 206 relate at least in part to the treatment or remediation of one or more Established Reasons 128. Table 200A also provides at least one record of a current Provider Location 208 for each Product 136/202. For at least one optional embodiment, the delivery modality 210 is also noted—i.e., V for vaporization, I for inhalation, E for edible, etc. . . .

For the present example these Established Reasons 128 are shown in the present example as Anxiety 212, Pain 214, Insomnia 216, Glaucoma 218, Inflammation 220, Attention 222, and Chronic Pain 224. It is specifically understood and appreciated that the list of constituents 206 may adjusted from time to time as additional constituents are identified, elevated in status, established reasons are refined, or other such elements are deemed beneficial to add, remove or refine for the enhancement of SDADP 100.

Beneath each Established Reason 128, exemplary table 200B shows three columns, the first is column 226 is the Effectiveness 140 (E), i.e. the effectiveness rating of the product for the Established Reason 128, the second column 228 is the Feedback 230 (F) provided by Users 102 based on their substantially contemporaneous reporting of how effectively the Product 136/202 satisfied their User Reason 124, and the third column 232 is the dosage 234 (D). Of course, in varying embodiments, additional columns may be provided to indicate different dosages for different modalities of delivery for the Product 136/202, different dosages for people of different weights/genders/age, and/or for such other data points as may be deemed relevant for different embodiments of SDADP 100.

It should further be noted that Table 200B permits the identification of a product being applicable to more than one Established Reason, each with potentially a different dosage—see for example Product 2 applicable for glaucoma at a dosage of 3 but also applicable for Inflammation at a dosage of 6.

The effectiveness 140 is at least in part based upon, and adjusted over time by the Feedback 230. For purposes of discussion these two values have been shown separately, but it is understood and appreciated that in varying embodiments, the effectiveness 140 may be adjusted substantially in real time in response to feedback 230. Alternatively, the feedback 230 may be buffered and averaged over a number of users, period of time, or other buffering element. In addition, various different weighting methods may be applied to determine by what value or degree the feedback 230 rating is used to adjust the effectiveness 140 rating.

With respect to Tables 200A and 200B, exemplary, notable levels for effectiveness, feedback and dosage have been shown in bold and an enlarged font for ease of identification. In varying embodiments, the levels of the reported constituents may be in percentages or levels according to a system best suited for the embodiment of SDADP 100 desired. Moreover, although constituents as percentages may be employed in some embodiments, for the examples presented herein, levels of the constituents as active elements are reported—as such, for ease of illustration and discussion, one compound may have two or more constituents with elevated levels to exemplify correlations to one or more Established Reasons even though the total values of all constituents will total over 100.

Returning to FIG. 2, it may be observed that Product 1 March 202A has a shown level of CBD as 81 and an effectiveness for anxiety of 74 which is the highest rating shown for all Products 136/202. Similarly, Product 1 June 202B has a shown level of CBD as 80 and an effectiveness rating for anxiety of 73 which is less than Product 1 March, however, Product 1 June 202B also has a shown effectiveness rating of 72 for Attention. Product 2 202C has a level of CBC as 50 and an effectiveness rating of 72 for Glaucoma. Product 3 202D has a level of Careen as 75 and a level of Pinene as 20 and an effectiveness rating of 65 for Insomnia. Product 4 202E has a level of CBC as 80 and an effectiveness rating of 78 for Chronic Pain. And Product 5 202F has a level of CBG as 20, a level of Pinene as 30 and a level of CBC as 20 and an effectiveness rating of 65 for Pain.

It should also be noted that Product 1 March 202A also has a shown level of Pinene as 23 and an effectiveness for Insomnia of 58 at a different dosage from that for anxiety, and this effectiveness for insomnia is second only to Product 3 202D. Similarly, Product 2 202C at a dosage of 6 has an effectiveness rating of 65 for inflammation.

Moreover, as shown in FIG. 3, SDADP 100 establishes a Correlation Tables 300 which advantageously correlates Established Reasons 128 with Constituents 138 and Products 136 having elevated levels of such correlated constituents 138. Moreover, as the number of Users 102 increases, and their feedback 230 is incorporated, SDADP 100 advantageously refines in precision to identify correlations between single constituents 138 and pluralities of constituents 138 with respect to Established Reasons 128. Indeed, as the tracking of a vast plurality of constituents is fully permitted and enabled by SDADP 100, subtle yet distinct relationships between slight differences in constituent levels or percentages will advantageously be realized over time.

Indeed, the Correlation Table 300 permits an understanding of the correlation of Constituents of a first Product to a first Established Reason may be greater than the correlation of Constituents of the first Product to a second Established Reason. Further, Correlation Table 300 may advantageously permit the identification of multiple constituents to correlate to one or more Established Reason more strongly than a single constituent alone.

With respect to the aggregation and processing of data, it is advantageously realistic to forecast that SDADP 100 will identify relationships between Constituents 138 and their correlations to Established Reasons 128 that are presently unknown, and upon identification may permit growers/producers to adjust crop strains and processing techniques in an effort to accentuate specific constituent properties of new Products 136/202 for specific Established Reasons 128.

Returning to FIG. 2 and more specifically table 200A and 200B, Product N 202G is presented as a new Product 136. As shown in table 200A the constituent levels for the exemplary constituents 138 are known, but the correlation of these constituent levels to Established Reasons 128 have not yet been entered into the Database of Products 134. However, based on the Correlation Table 300 in FIG. 3, it may be advantageously predicted that Product N 202G having a high level of CBD (shown as 92) will be beneficial for Anxiety, having a high level of Pinene (shown as 32) will be beneficial for Pain, and having a high level of CBC (shown as 75) will be beneficial for Chronic Pain.

More specifically, for at least one embodiment of the present invention, known correlations of Constituents 138 to Established Reasons 128 for known Products 136/202 permits a predicted correlation of Constituents 138 to Established Reasons 128 for new Products, e.g. Product 202G.

Of course, as Product N 202G is new the dosage values have not yet been established, however SDADP 100 may implement an initialization protocol of averaging the known dosage values for each of the known modalities of delivery so as to provide an initial dosage for Product N 202G. For the present example, new Product 202G is initialized with the same values for effectiveness and dosage as present for Products 136 having similar constituent levels.

Further, it should be understood and appreciated that Correlation Table 300 may also identify combinations of constituents that are detrimental to one or more Established Reasons 128. Moreover, user Feedback may establish that high levels of CBC and Pinene in combination are not beneficial for general Pain, but are fine for Chronic Pain. Moreover, as part of the feedback gathering process, for at least one embodiment, SDADP 100 requests Users 102 to provide feedback regarding Established Reasons other than the User Reason for which their dosage was requested. In so doing, SDADP 100 further confirms and refines known correlations and may identify new correlations.

Having described embodiments for SDADP 100 as shown with respect to FIGS. 1, 2 and 3, other embodiments relating to varying methods of determining appropriate dosage for a product will now be discussed with respect to FIG. 4 in connection with FIGS. 5-8. Moreover, FIGS. 5-8 are variations based on FIG. 1 illustrating a User Request for specific Users 102 and the resulting dosage provided by SDADP 100. It will be appreciated that the described method need not be performed in the order in which it is herein described, but that this description is merely exemplary of one method of determining appropriate dosage for a product in accordance with the present invention.

Example No. 1—Request for Product Based on User Reason

Figure 4:
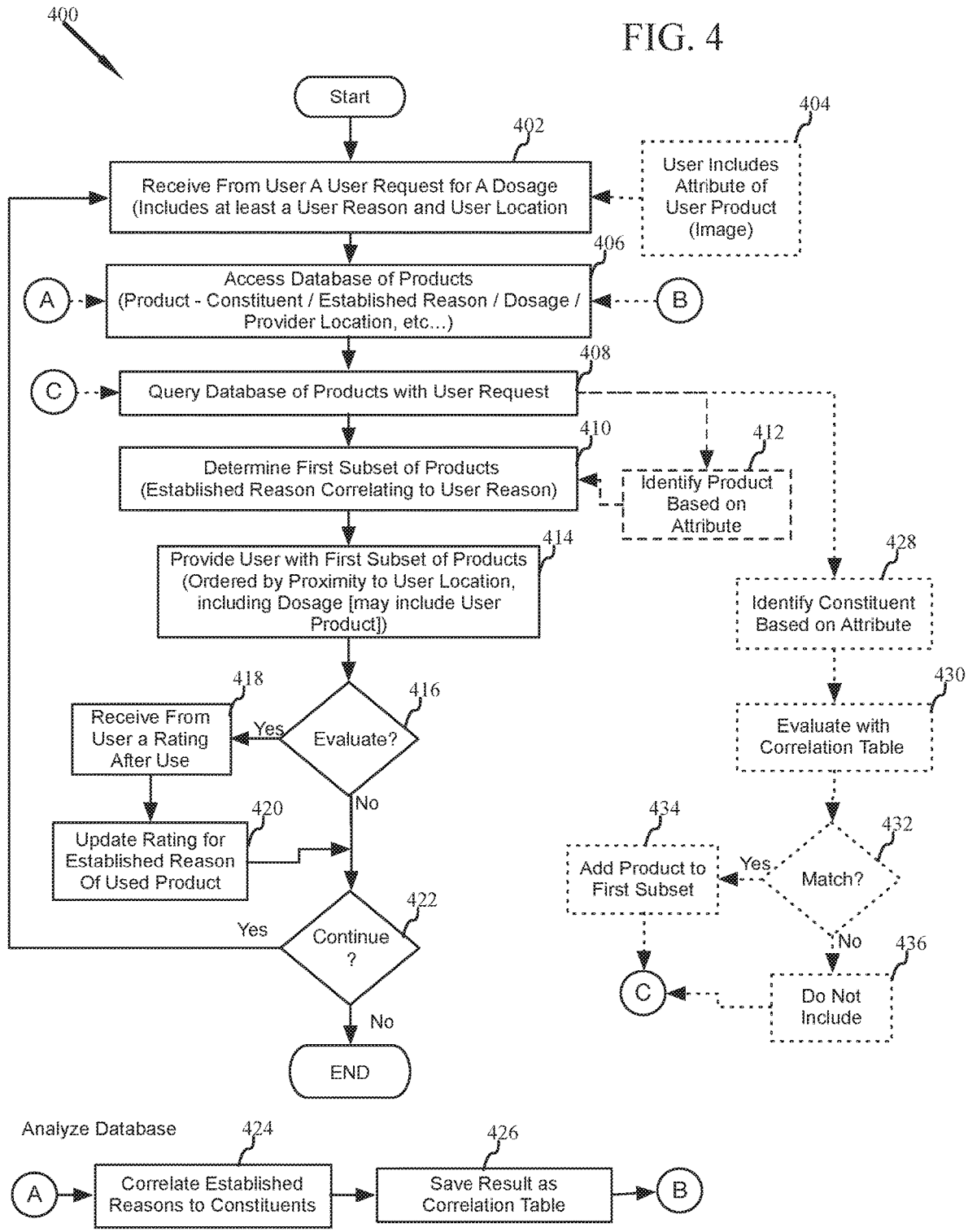
FIG. 4 illustrates a flow diagram for determining an appropriate dose of a product in accordance with at least one embodiment.
Figure 5:
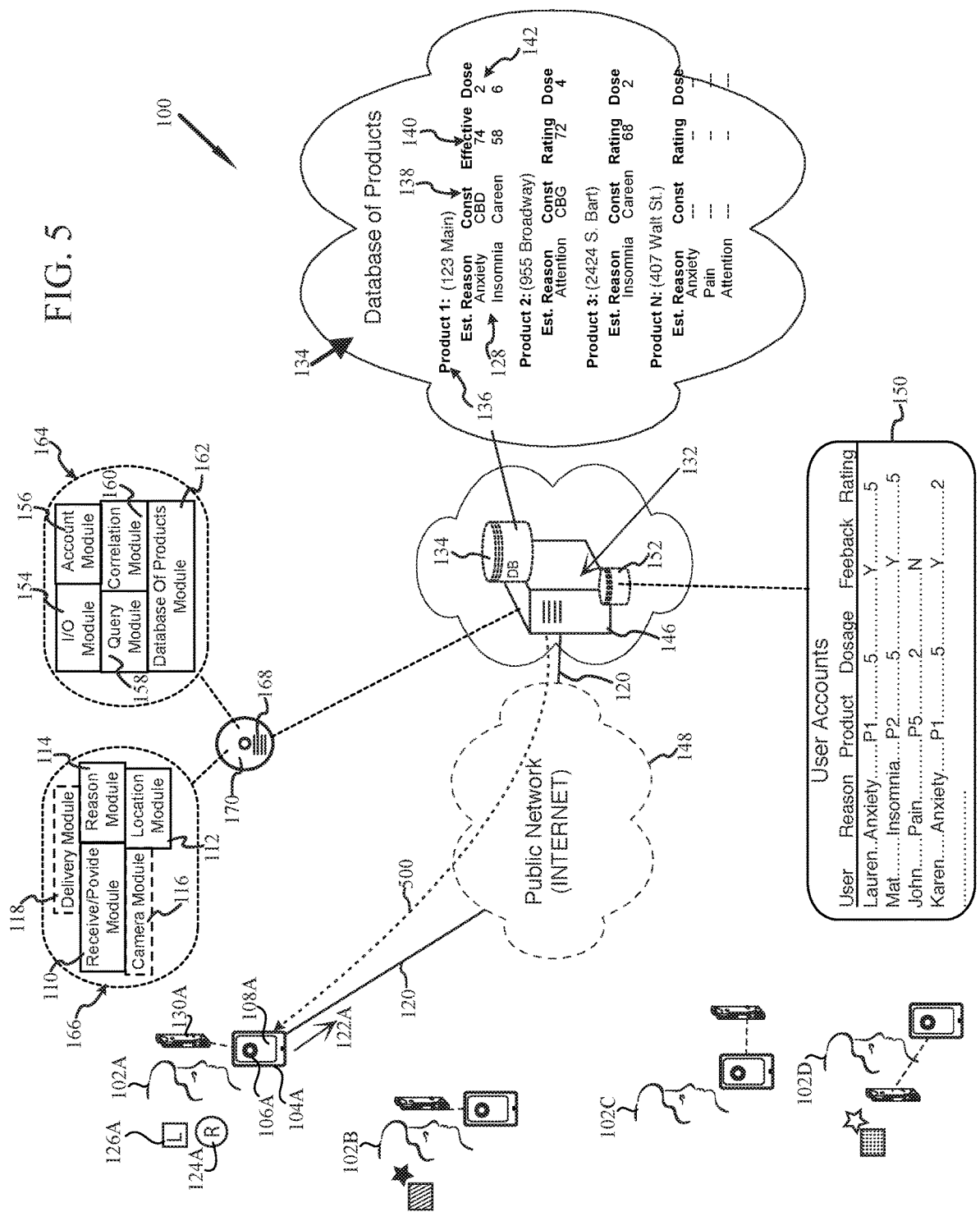
FIG. 5-8 are refined versions of FIG. 1 further illustrating a specific example of determining an appropriate dose of a product in accordance with at least one embodiment.
Figure 6:
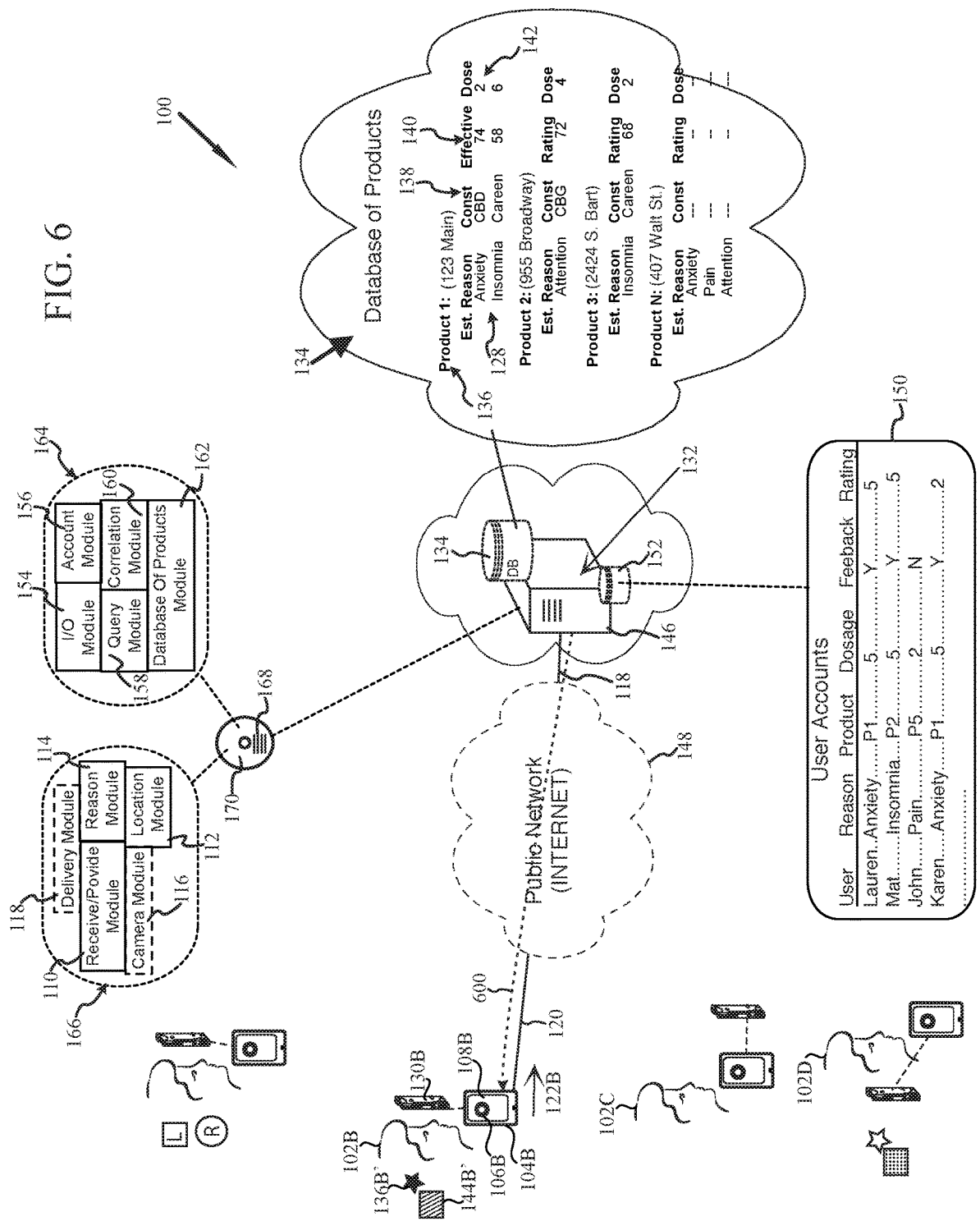

As shown in FIG. 4, method 400 typically begins with SDADP 100 receiving from a User 102 a Request 122A for a dosage, block 402. With respect to FIG. 5, this exemplary first case regards User 102A. For the sake of discussion, the indicated User Reason 124 is Anxiety, and the User's location is 945 Broadway. As will be discussed below, for at least one optional case, the User 102 may provide at least one attribute of a User Product 136', optional block 404.

The method proceeds by accessing the Database of Products 134, block 406. Although it is typical for systems utilizing databases to proactively implement measures to simplify searching for speed and accuracy, in some cases it may be desirable to query the entire database in substantially real time, block 408.

Method 400 thus determines that in terms of correlation to effectiveness for Anxiety the subset of identified products is Product 1 202A first, Product 1 202B second, and product 2 202C third, block 410, as a first subset of Products, block 410.

The method continues by reviewing the User's location with respect to the Provider Locations having the Products of the first subset. For the purposes of this example, the User Location is 945 Broadway, so Product 1 shown to be at 955

Broadway is presumed 0.25 miles away. It will be further understood that 123 Main is 6 miles away and 420 East Green is 12 miles away.

As such Product 1 June is ranked $1^{st}$ based on proximity, Product 1 March is ranked $2^{nd}$ based on proximity, and Product 2 is ranked $3^{rd}$ based on proximity. This subset of the Products is returned to the User along with the appropriate dosage and efficiency, block 414 and transmission 500 in FIG. 5. As such, the User may self-determine whether or not the close proximity of Product 1 June is preferred over the location of Product 1 March, even though Product 1 March has a slightly higher effectiveness score.

For embodiments of the present invention, the User 102 selected Product 136 from the first subset of Products 136 is understood and appreciated as the selected product. It is this selected product 136 that is used by the User 102, and this selected product 136 for which SDADP 100 will seek User feedback in an ongoing and advantageous strategy to refine correlations between Products 136 and Established Reasons 128.

For at least one embodiment, SDADP 100 notes the time that the determination of first subset of products was communicated back to User 102A, and as such initiates a timer to follow-up with User 102 for an evaluation, decision 416. For at least one alternative embodiment, as noted above the dosage device 130A may be in wireless communication with the User's first device 108A and as such, SDADP 100 receives an automated notification when User 102 has administered the dosage, as well as optionally the actual dosage administered. As such, SDADP 100 can initiate a precise timer for feedback follow-up based on notification of when the dosage was administered.

When the timer has elapsed, or upon some other relevant trigger event, method 400 contacts the User 102A by way of his or her first device 104A and request feedback as to the effectiveness of the Product and dosage for the User Reason 124. Additional feedback data may also be obtained.

Moreover, for the present example it is presumed that User 102A complies with the request for feedback and provides a rating after use, block 418. Accordingly, SDADP 100 updates the rating for the Established Reason, 420. It will be appreciated that in varying embodiments, SDADP 100 may employ different methodologies or weighting factors so that the overall rating of the established reason is refined, it is not likely to be dramatically affected by an erroneous rating, or an intentionally overly high or low rating.

Following such an update, method 400 continued with the basic decision to continue or not, decision 422.

As noted above, for at least one embodiment, SDADP 100 automatically analyzes the Database of Products so as to establish the Correlation Tables 300 shown in FIG. 3. In varying embodiments, such automatic analysis may be performed at time intervals, following each submission of user feedback, upon the addition/deletion/modification of a Product record, or upon such other trigger or event as is deemed appropriate for a given instance of SDADP 100. Accordingly, for at least one embodiment, method 400 shows optional block 424 and 426 for the actions of correlating Established Reasons to Constituents, block 424, and saving the results as a Correlation Table 300, block 426.

Example No. 2—Request Based on User Reason, with Attribute from User Product

As also noted above, optionally, at pre-determined trigger events such as but not limited to time intervals, User 102 feedback responses, the addition of a new Product 136, the modification of a record associated with a Product 136, or other event, SDADP 100 will query the Database of Products 134 to correlate Established Reasons 128 to Constituents 138, block 424, and thereby develop the Correlation Table 300, block 426.

Further, a User Request 122 may include at least one Attribute 144 from a User Product 136'. With respect to FIG. 6, this exemplary second case regards User 102B. As shown, User 102B has User Product 136B' and has obtained Attribute 144B through the use of the camera module to capture an image of constituent listing on the label, a bar code, QR code or other element that may be used for specific identification. For the sake of discussion, the indicated User Reason 124B is Inflammation, and the User's location is 100 Main.

For this optional case, in addition to providing Request (block 402), User 102B includes an Attribute (i.e., the image of at least a portion of User Product 136B'), block 404. For the present example, the Attribute is a unique identifier previously suppled to SDADP 100 by the product manufacturer, thus upon receipt of the Attribute and more specifically the unique identifier the User Product 136' may be specifically identified as a known Product, e.g., Product 3 202D.

In this case, Product 3 202D is not shown to correlate strongly to Inflammation—the effectiveness score is shown as a 1. Accordingly, method 300 proceeds to review the database, and/or the Correlation Table to identify a first subset of Products that do correlate to the Established Reason of Inflammation 202—which results in first subset of Product 1 March 202A and Product 2 202D.

The User's location of 407 Walt St. is compared to 123 Main and 420 East Green, and for purposes of this example it is assumed that 123 Main is deemed closer. Product 2 is listed first followed by Product 1 March even though both are available at the same location, communication 600 in FIG. 6, block 414 in FIG. 4.

Continuing with this example, it is further understood that User 102B has a dosage device 130 in communication with the Dosing System 132 such SDADP 100 is informed that User 102B selected Product 1 March with a dosage of 3 over Product 2 requiring a dosage of 6. This information was obtained by dosage device 130 using a detector to detect the reservoir of product and noting the dosage setting selected by User 102B.

After thirty minutes following administration of the dosage, SDADP 100 triggers an evaluation event, decision 416, and User 102B responds with a rating of 5, which is in turn used by SDADP 100 to update the Rating of the Established Reason of Inflammation for Product 1 March, block 420.

Example No. 3—Request Based on User Reason and Preferred Modality of Delivery

Figure 7:
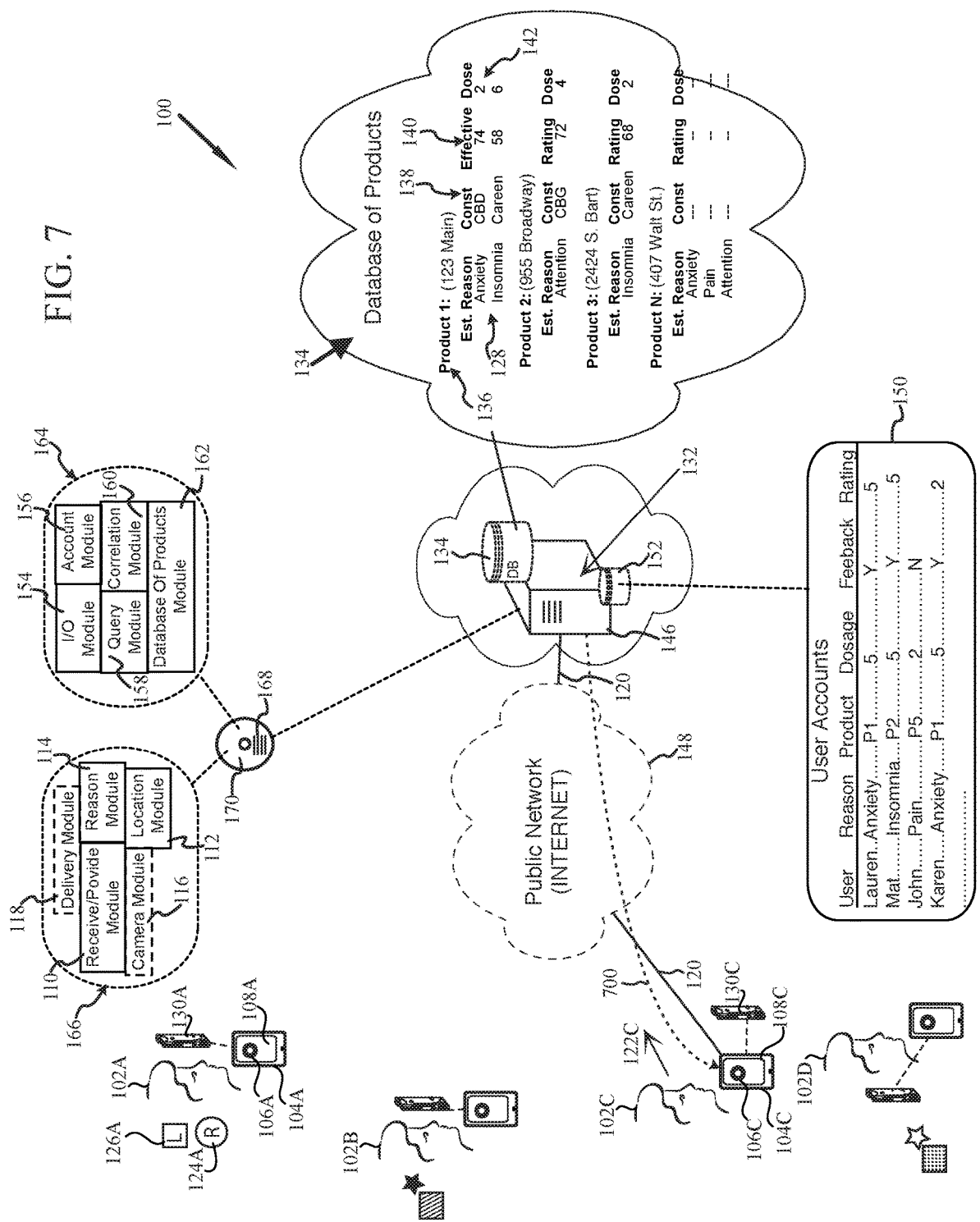

With respect to FIG. 7, this exemplary third case regards User 102C. For the sake of discussion, the indicated User Reason 124C is Insomnia, and the User's location is 221 B. Baker Street. In addition, User 102C has also requested a delivery modality of "edible."

In querying the Database of Products 134, and/or the Correlation Table, SDADP 100 determines that Product 1 March and Product 3 both have a high correlation to Insomnia, block 408. Further, for this optional embodiment, in response to the preference of "edible" SDADP 100 notes that only Product 3 is available in an edible form. The first subset of Products therefore only includes Product 3, available at 2424 S. Bart, and with a dosage of 3 units, transmission 700 in FIG. 7.

Upon acquisition of the removable reservoir of Product 3 providing edible elements, User 102C couples the reservoir to the dosage device 130 and receives 3 edible units, which are in turn reported to SDADP 100, and more specifically the Dosing System 132.

For the purposes of this example, it is presumed that the dosage for insomnia has been effective such that upon polling for feedback, decision 416, User 102C is not responsive and no feedback that is contemporaneous to the dosing event is gathered.

Example No. 4—Request Based on User Reason with Attribute of User Product

Similar to Example 2 above, this exemplary fourth case regards User 102D. As shown, User 102D has User Product 136D' and has obtained Attribute 144D through the use of the camera module to capture an image of constituent listing on the label, a bar code, QR code or other element that may be used for specific identification. For the sake of discussion, the indicated User Reason 124D is Chronic Pain, and the User's location is 1313 Mockingbird Lane.

For this optional case, in addition to providing Request (block 402), User 102D includes an Attribute (i.e., the image of at least a portion of User Product 136D'), block 404. For this example, no unique identifier is present, so User 102D has provided a picture showing the reported constituents and their concentrations.

As User Product 136D', now identified as Product N 202G, does not uniquely identify, upon accessing the database, SDADP 100 identifies at least one constituent and reported level from the attribute provided. From the attribute, SDADP 100 determines that Product N 202G has an 82 level CBD, a 20 level Pinene and a 75 level CBC, optional block 428. These determined levels of constituents are then evaluated with Constituent Table for correlation to Established Reasons which in turn are evaluated to the User Reason, optional block 430.

Upon comparing these elevated levels with the other exemplary Products in the Database of Products 134, SDADP 100 extrapolates that Product N 202G is likely to have high correlations of effectiveness to Anxiety, Pain and Chronic Pain, optional decision 432. As the Established Reason of Chronic Pain corresponds to the User Reason 124D of "chronic pain", Product N 202G is added to the first subset of products, optional block 434. Had no correlation been determined with respect to an Established Reason, Product N 202G would not be added to the first subset, optional block 436. It is understood and appreciated that method 400 may continue to query for additional Products so as to provide User 102D with greater options and potential effectiveness.

Figure 8:
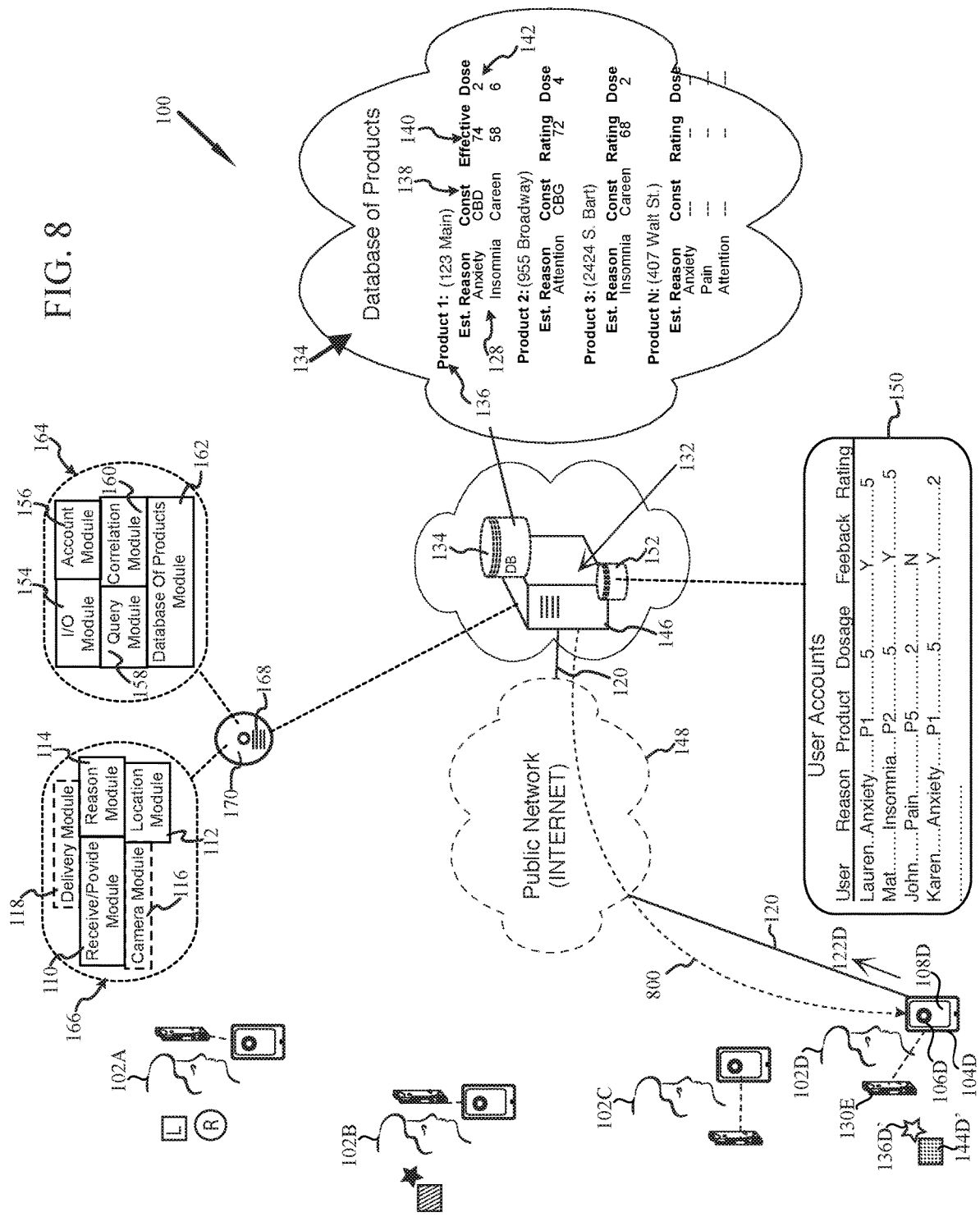

As with the above examples, this first subset is communicated back to User 102D as transmission 800, FIG. 8. Moreover, for the present example, SDADP 100 has determined that the user Product 136D' is effective for the User Reason as a projected dose determined by comparison with other Products. In the case of a topical product such as a cream, SDADP 100 may provide the user with dosage that they may self administer from the product container directly. In other embodiments, the user may have a dosing device 130D which is used to administer the determined dosage.

As is shown table 200, Product N 202G has been added and upon feedback from User 102D the process of refinement of effectiveness will progress as with the other Products known to SDADP 100.

Further, based on these levels and correlated predictions, SDADP 100 establishes an initial dosage as substantially the same as the other known Products correlating to such Established Reasons.

To summarize from the above, for at least one embodiment, provided is a method 400 of determining an appropriate dose 142 of a Product 136, including: using a first instance of an application on a first user computing device 104 for receiving from a User 102 a User Request 122 for a Dosage 142, the User Request 122 including at least a User Reason 124 and a User Location 126, the first instance of the application accessing a remote first server system having a processor and a Database of Products 134, each Product 136 having at least one Constituent, at least one Established Reason 128, a Dosage 142 for each Established Reason 128, and Provider Location, the Database of Products 134 further having a Correlation Table 300 correlating Established Reasons 128 to Constituents 138; querying the Database of Products 134 with the User Request 122 to determine at least a first subset of Products having the at least one Established Reason 128 correlating to the User Reason 124; providing the first user computing device 104 with the first subset of Products 136 arranged by proximity of the Provider Location to the User Location 126, the first subset of Products 136 further including the Dosage 142 for each Product 136 in the first subset of Products 136.

Figure 9:
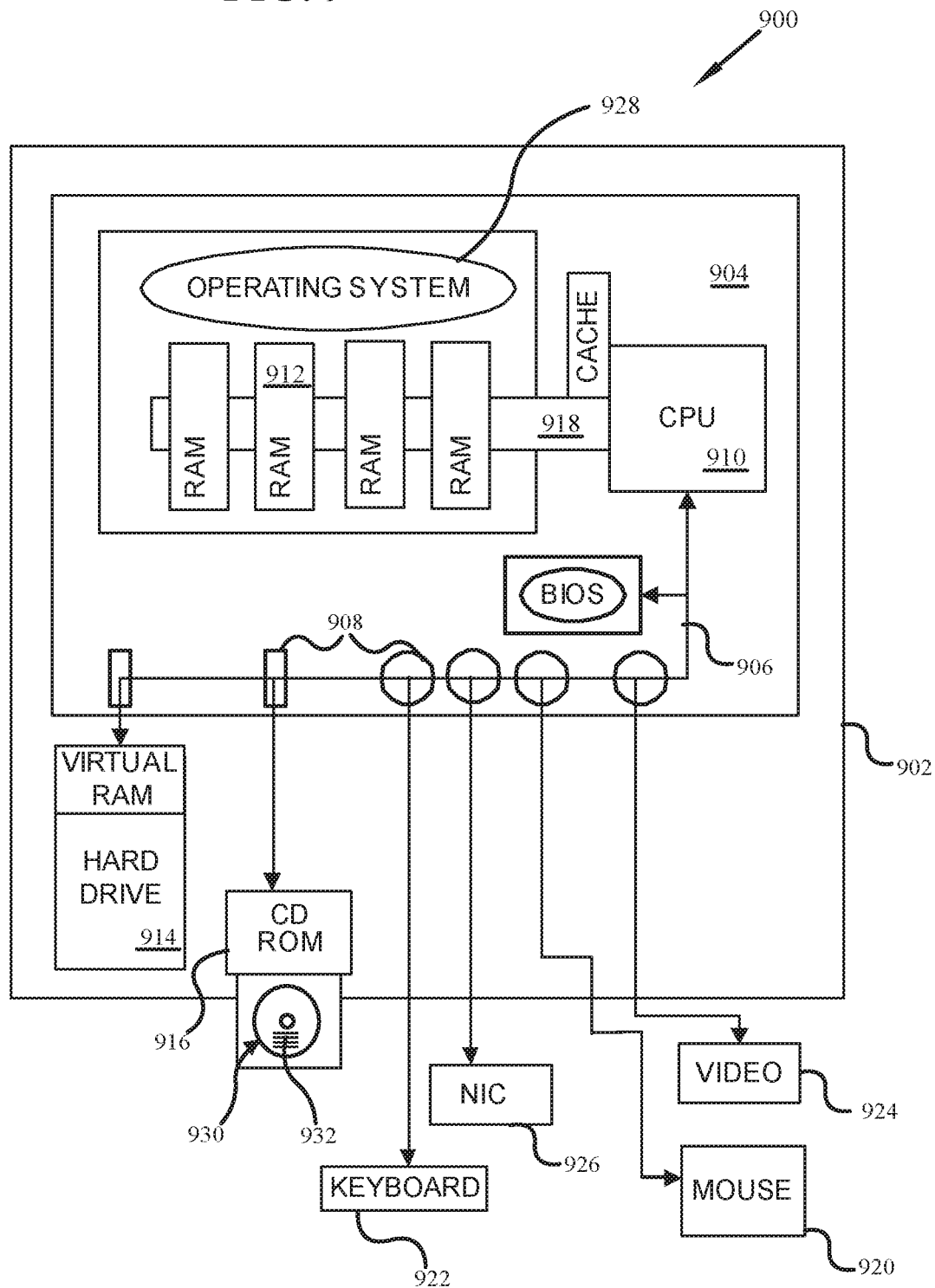
FIG. 9 is a high level block diagram of a computer system in accordance with at least one embodiment.

To expand upon the initial suggestion of at least the First Device 104, dosage device 130, Dosing System 132, Database of Products 134 and other systems comprising SDADP 100 being computer systems adapted to their specific roles, FIG. 9 is a high level block diagram of an exemplary computer system 900 such as may be provided for one or more of the elements comprising at least the First Device 104, dosage device 130, Dosing System 132, Database of Products 134 whether provided as distinct individual systems or integrated together in one or more computer systems.

Computer system 900 has a case 902, enclosing a main board 904. The main board 904 has a system bus 906, connection ports 908, a processing unit, such as Central Processing Unit (CPU) 910 with at least one microprocessor (not shown) and a memory storage device, such as main memory 912, hard drive 914 and CD/DVD ROM drive 916.

Memory bus 918 couples main memory 912 to the CPU 910. A system bus 906 couples the hard disc drive 914, CD/DVD ROM drive 916 and connection ports 908 to the CPU 910. Multiple input devices may be provided, such as, for example, a mouse 920 and keyboard 922. Multiple output devices may also be provided, such as, for example, a video monitor 924 and a printer (not shown). As computer system 900 is intended to be interconnected with other computer systems in the CSE 100 a combined input/output device such as at least one network interface card, or NIC 926 is also provided.

Computer system 900 may be a commercially available system, such as a desktop workstation unit provided by IBM, Dell Computers, Gateway, Apple, or other computer system provider. Computer system 900 may also be a networked computer system, wherein memory storage components such as hard drive 914, additional CPUs 910 and output devices such as printers are provided by physically separate computer systems commonly connected together in the network.

Those skilled in the art will understand and appreciate that the physical composition of components and component interconnections are comprised by the computer system 900, and select a computer system 900 suitable for one or more of the computer systems incorporated in the formation and operation of CSE 100.

When computer system 900 is activated, preferably an operating system 928 will load into main memory 912 as part of the boot strap startup sequence and ready the computer system 900 for operation. At the simplest level, and in the most general sense, the tasks of an operating system fall into specific categories, such as, process management, device management (including application and User interface management) and memory management, for example. The form of the computer-readable medium 930 and language of the program 932 are understood to be appropriate for and functionally cooperate with the computer system 900.

Moreover, variations of computer system 900 may be adapted to provide the physical elements of one or more components comprising each at least the First Device 104, dosage device 130, Dosing System 132, Database of Products 134, the switches, routers and such other components as may be desired and appropriate for the methods and systems for determining an appropriate dose of a product as set forth above.

Changes may be made in the above methods, systems and structures without departing from the scope hereof. It should thus be noted that the matter contained in the above description and/or shown in the accompanying drawings should be interpreted as illustrative and not in a limiting sense. Indeed, many other embodiments are feasible and possible, as will be evident to one of ordinary skill in the art. The claims that follow are not limited by or to the embodiments discussed herein, but are limited solely by their terms and the Doctrine of Equivalents.

What is claimed:

1. A method of determining an appropriate Product and dosage of the Product to treat a specified ailment, comprising:
    receiving from a User by way of a user computing device having a processor directing wireless transmission by way of a transceiver a User Request for a Product to treat a specified ailment, the User Request including at least a User Reason and a User Location;
    the user requested evaluated by a database processor accessing a dynamic Database of Products, each product having a plurality of Constituents and a ratio of Constituents correlated to at least one Established Reason, the correlations between the ratio of Constituents and Established Reasons established and adjusted in substantially real time by user feedback transmitted to the database processor to quantifiably associate the current effectiveness of each Product to the at least one Established Reason, the Database of Products further providing specific information for each Product including a Dosage for each Established Reason and Provider Location;
    the database processor querying the dynamic Database of Products with the User Request to determine at least a first subset of Products having the at least one Established Reason correlating to the User Reason based upon a correlation of the ratio of Constituents to each Established Reason, the User Reason correlated to the Established Reasons, each Product in the first subset of Products thereby identified to treat the specified ailment based on ratio of Constituents correlating to the User Reason;
    the database processor providing the user computing device with the first subset of Products identified to treat the specific ailment, the processor of the user computer device rendering upon a display the first subset of Products displayed by proximity of the Provider Location to the User Location as determined by the processor utilizing a location determining system, the first subset of Products further including the Dosage for each Product in the first subset of Products to treat the specified ailment; and
    upon the user selecting a Product from the first subset of Products, the user computing device directing a vaporizing metered dosing device to administer the Dosage of the selected Product to the User, the vaporizing metered dosing device comprising:
        a housing at least partially enclosing,
            a removable cartridge received within the housing and configured to store a predefined quantity of concentrate therein the cartridge comprising an identification code associated with the concentrate, and a plunger structured and arranged to extrude concentrate from the cartridge;
            a communication unit disposed within the housing, the communication unit configured to transmit the identification code to the user computing device,
            a dosing unit located in the housing and operatively coupled with the cartridge, the dosing unit configured to engage the plunger to extrude a known quantity of the concentrate from the cartridge;
            a vaporization chamber defined in the housing and in fluid communication with the cartridge, the vaporization chamber configured to collect the concentrate extruded from the cartridge, the vaporization chamber being disposed physically separate from the cartridge;
            a heating element in thermal communication with the vaporization chamber, the heating element configured to generate heat energy to vaporize the concentrate in the vaporization chamber; and
            a control unit disposed within the housing and configured to read the identification code from the cartridge, the control unit further configured to control the heat energy generated by the heating element based on the identification code of the cartridge; and
    the user computing device collecting and returning to the database processor real time quantified feedback from the user.

2. The method of claim 1, wherein the Constituents are at least one cannabinoid.

3. The method of claim 2, wherein the at least one cannabinoid is selected from the group consisting of: THC, THC-A, CBN, CBG, CBC, CBD, CBD-A, THCV, and CBDV.

4. The method of claim 1, wherein the Constituents are at least one terpene.

5. The method of claim 4, wherein the at least one terpene is selected from the group consisting of: Alpha-Ocimene, Beta-Ocimene, Camphene, Careen, Caryophyllene, Carophyllene oxide, Cymene, Eucalyptol, Isopulefgol, Limonene, Linalool, Myrcene, Pinene, Terpinine, Terpinolene.

6. The method of claim 1, wherein the User Reason and the Established Reason are selected from the group consisting of: acute pain, anxiety, arthritis, cancer, chronic pain, focused attention, glaucoma, inflammation, insomnia, multiple sclerosis (MS), pain, relaxation, stress, sleepiness, treatment of tremors.

7. The method of claim 1, further including analyzing the dynamic Database of Products to determine a Correlation Table for Established Reasons to Constituents.

8. The method of claim 7, wherein the Correlation Table is consulted to provide the first subset of Products.

9. The method of claim 7, wherein two or more Constituents of a Product correlate to an Established Reason.

10. The method of claim 7, wherein the correlation of Constituents of a first Product to a First Established Reason are greater than the correlation of Constituents of the first Product to a Second Established Reason.

11. The method of claim 7, wherein the correlation of the plurality of Constituents of a First Product to a First Established Reason are greater than the correlation of a single Constituent of a Second Product to the First Established Reason.

12. The method of claim 7, wherein the User Request further includes an Attribute of a User Product, the Attribute identifying at least one User Product Constituent associated with the User Product, and querying the Correlation Table to determine a correlation between the User Product Constituent and the User Reason by comparison to correlation of Established Reasons to Constituents of Products in the dynamic Database.

13. The method of claim 7, wherein subsequent to use of a selected Product from the first subset of Products, the User providing a quantified rank of effectiveness of the selected Product in alleviating the specified ailment, the Correlation Table adjusted by this feedback to further improve the correlation of the Established Reason to the Constituents of the selected Product.

14. The method of claim 1, wherein the Request further includes an Attribute of a User Product.

15. The method of claim 14, wherein the Attribute of the User Product is determined by scanning the User Product, the scan compared with Products of the dynamic Database to identify at least one Constituent, at least one Established Reason, and a Dosage for the Established Reason correlating to the User Product, and in response to a correlation between the User Reason and the Established Reason associated with the User Product, providing the User with a Dosage.

16. The method of claim 14, wherein the Attribute of the User Product is determined by an Image of the User Product, the Image compared with Products of the dynamic Database to identify at least one Constituent, at least one Established Reason, and a Dosage for the Established Reason correlating to the User Product, and in response to a correlation between the User Reason and the Established Reason associated with the User Product, providing the User with a Dosage.

17. The method of claim 1, wherein each Product further has a Use Rating for each Established Reason.

18. The method of claim 17, further including receiving from the User a Rating after use of a Chosen Product selected from the first subset of Products, and updating the User Rating for the Established Reason correlating to the User Reason of the Chosen Product.

19. The method of claim 1, wherein the initial correlation of the ratio of Constituents each Product to each Established Reason is established by User feedback providing quantified rank of effectiveness on the use of a selected Product for one of the Established Reasons.

20. A method of determining an appropriate Product and dosage of the Product to treat a specified ailment, comprising:

using a first instance of an application on a first user computing device having a processor directing at least a memory, a transceiver, a display, and a location system for receiving from a User a User Request for a Product to treat a specified ailment, the User Request including at least a User Reason and a User Location, the first instance of the application directing the processor to wirelessly transmit by way of the transceiver the User Request to a remote first server system having a database processor and a dynamic Database of Products, each product having a plurality of Constituents and a ratio of Constituents correlated to least one Established Reason, the correlations between the ratio of Constituents and Established Reasons established and adjusted in substantially real time by user feedback transmitted to the database processor to quantifiably associate the current effectiveness of each Product to the at least one Established Reason, the Database of Products further providing specific information for each Product including a Dosage for each Established Reason, and Provider Location;

the database processor querying the dynamic Database of Products with the User Request to determine at least a first subset of Products having the at least one Established Reason correlating to the User Reason based upon a correlation of: the ratio of Constituents to each Established Reason, the User Reason correlated to the Established Reasons, each Product in the first subset of Products thereby identified to treat the specified ailment based on ratio of Constituents correlating to the User Reason;

the database processor providing the user computing device with the first subset of Products identified to treat the specific ailment the processor of the user computing device rendering upon a display the first subset of Products displayed by proximity of the Provider Location to the User Location as determined by the processor utilizing a location determining system, the first subset of Products further including the Dosage for each Product in the first subset of Products to treat the specified ailment; and upon the user selecting a Product from the first subset of Products, the user computing device directing a vaporizing metered dosing device to administer the Dosage of the selected Product to the User, the vaporizing metered dosing device comprising:

a housing at least partially enclosing,
    a removable cartridge received within the housing and configured to store a predefined quantity of concentrate therein the cartridge comprising an identification code associated with the concentrate, and a plunger structured and arranged to extrude concentrate from the cartridge;
    a communication unit disposed within the housing, the communication unit configured to transmit the identification ode to the user computer device,
    a dosing unit located in the housing and operatively coupled with the cartridge, the dosing unit configured to engage the plunger to extrude a known quantity of the concentrate from the cartridge;
    a vaporization chamber defined in the housing and in fluid communication with the cartridge, the vaporization chamber configured to collect the concentrate extruded from the cartridge, the vaporization chamber being disposed physically separate from the cartridge;

a heating element in thermal communication with the vaporization chamber, the heating element configured to generate heat energy to vaporize the concentrate in the vaporization chamber; and a control unit disposed within the housing and configured to read the identification code from the cartridge, the control unit further configured to control the heat energy generated by the heating element based on the identification code of the cartridge; and the user computing device collecting and returning to the database processor real time quantified feedback from the user.

21. The method of claim 20, wherein the Constituents are at least one cannabinoid.

22. The method of claim 21, wherein the at least one cannabinoid is selected from the group consisting: THC, THC-A, CBN, CBG, CBC, CBD, CBD-A, THCV, CBDV.

23. The method of claim 20, wherein the Constituents are at least one terpene.

24. The method of claim 23, wherein the at least one terpene is selected from the group consisting of: Alpha-Ocimene, Beta-Ocimene, Camphene, Careen, Caryophyllene, Carophyllene oxide, Cymene, Eucalyptol, Isopulefgol, Limonene, Linalool, Myrcene, Pinene, Terpinine, Terpinolene.

25. The method of claim 20, wherein the User Reason and the Established Reason are selected from the group consisting of: acute pain, anxiety, arthritis, cancer, chronic pain, focused attention, glaucoma, inflammation, insomnia, multiple sclerosis (MS), pain, relaxation, stress, sleepiness, treatment of tremors, cancer.

26. The method of claim 20, wherein the Correlation Table is consulted to provide the first subset of Products.

27. The method of claim 20, wherein the User Request further includes an Attribute of a User Product.

28. The method of claim 27, wherein the User Request further includes an Attribute of a User Product, the Attribute identifying at least one User Product Constituent associated with the User Product, and querying the Correlation Table to determine a correlation between the User Product Constituent and the User Reason by comparison to correlation of Established Reasons to Constituents of Products in the dynamic Database.

29. The method of claim 27, wherein the Attribute of the User Product is determined by scanning the User Product, the scan compared with Products of the dynamic Database to identify at least one Constituent, at least one Established Reason, and a Dosage for the Established Reason correlating to the User Product, and in response to a correlation between the User Reason and the Established Reason associated with the User Product, providing the User with a Dosage.

30. The method of claim 27, wherein the Attribute of the User Product is determined by a photo of the User Product, the photo compared with Products of the dynamic Database to identify at least one Constituent, at least one Established Reason, and a Dosage for the Established Reason correlating to the User Product, and in response to a correlation between the User Reason and the Established Reason associated with the User Product, providing the User with a Dosage.

31. The method of claim 20, wherein each Product further has a Use Rating for each Established Reason.

32. The method of claim 31, further including receiving from the User a Rating after use of a Chosen Product selected from the first subset of Products, and updating the User Rating for the Established Reason correlating to the User Reason of the Chosen Product.

33. The method of claim 20, wherein subsequent to use of a selected Product from the first subset of Products, the User providing a quantified rank of effectiveness of the selected Product in alleviating the specified ailment, the Correlation Table adjusted to further improve the correlation of the Established Reason to the Constituents of the selected Product.

34. The method of claim 20, wherein the initial correlation of the ratio of Constituents of each Product to each Established Reason is established by User feedback providing quantified rank of effectiveness on the use of a selected Product for one of the Established Reasons.

35. A system for determining appropriate Product and dosage of the Product to treat a specified ailment, comprising:

a remote server system having a database processor and a dynamic Database of Products, each product having a plurality of Constituents and a ratio of Constituents correlated to at least one Established Relation, the correlations between the ratio of Constituents and Established Reasons established and adjusted in substantially real time by user feedback transmitted to the database processor to quantifiably associate the current effectiveness of each Product to the at least one Established Reason, the Database of Products further providing specific information for each Product including a Dosage for each Established Reason and Provider Location;

at least one remote Application for adapting a user computing device for determining an appropriate Product and corresponding dosage to treat a specified ailment, for installation upon a remote computing device having a processor, at least a memory, a transceiver, a display and a location system, the remote application adapting and directing the processor for wireless communication with the remote server to provide a User Request for a Product to treat a specified ailment, the User Request including at least a User Reason and a User Location, the database processor of the of remote server system further structured and arranged to query the dynamic Database of Products with the User Request to determine at least a first subset of Products having the at least one Established Reason correlating to the User Reason based upon a correlation of the ratio of Constituents to each Established Reason, the User Reason correlated to the Established Reasons, each Product in the first subset of Products thereby identified to treat the specified ailment based on ratio of Constituents correlating to the User Reason, the processor of the user company device rendering upon a display the first subset of Products displayed by proximity of the Provider Location to the User Location, the first subset of Products further including the Dosage for each Product in the first subset of Products to treat the specified ailment; and a vaporizing metered dosing device comprising:
a housing at least partially enclosing;
a removable cartridge received within the housing and configured to store a predefined quantity of concentrate, and a plunger structured and arranged to extrude concentrate from the cartridge;
a communication unit disposed within the housing, the communication unit configured to transmit the identification code to the user computer device, a dosing unit located in the housing and operatively coupled with the cartridge, the dosing unit configured to engage the plunger to extrude a known quantity of the concentrate from the cartridge;

a vaporization chamber defined in the housing and in fluid communication with the cartridge the vaporization chamber configured to collect the concentrate extruded from the cartridge the vaporization chamber being disposed physically separate from the cartridge, a heating element in thermal communication with the vaporization chamber, the heating element configured to generate heat energy to vaporize the concentrate in the vaporization chamber and a control unit disposed within the housing and configured to read the identification code from the cartridge, the control unit further configured to control the heat energy generated by the heating element based on the identification code of the cartridge, wherein the user computing device directing the vaporizing metered dosing device to administer the Dosage of a Product from the first subset of Products to the User, and collecting and returning to the database processor real time quantified feedback from the user.

36. The system of claim 35, wherein the Constituents are at least one cannabinoid.

37. The system of claim 36, wherein the at least one cannabinoid is selected from the group consisting of: THC, THC-A, CBN, CBG, CBC, CBD, CBD-A, THCV, CBDV.

38. The system of claim 35, wherein the Constituents are at least one terpene.

39. The system of claim 38, wherein the at least one terpene is selected from the group consisting: of Alpha-Ocimene, Beta-Ocimene, Camphene, Careen, Caryophyllene, Carophyllene oxide, Cymene, Eucalyptol, Isopulefgol, Limonene, Linalool, Myrcene, Pinene, Terpinine, Terpinolene.

40. The system of claim 35, wherein the User Reason and the Established Reason are selected from the group consisting of: acute pain, anxiety, arthritis, cancer, chronic pain, focused attention, glaucoma, inflammation, insomnia, multiple sclerosis (MS), pain, relaxation, stress, sleepiness, treatment of tremors, cancer.

41. The system of claim 35, wherein the Correlation Table is consulted to provide the first subset of Products.

42. The system of claim 35, wherein the User Request further includes an Attribute of a User Product.

43. The system of claim 42, wherein the User Request further includes an Attribute of a User Product, the Attribute identifying at least one User Product Constituent associated with the User Product, and querying the Correlation Table to determine a correlation between the User Product Constituent and the User Reason by comparison to correlation of Established Reasons to Constituents of Products in the dynamic Database.

44. The system of claim 42, wherein the Attribute of the User Product is determined by scanning the User Product, the scan compared with Products of the dynamic Database to identify at least one Constituent, at least one Established Reason, and a Dosage for the Established Reason correlating to the User Product, and in response to a correlation between the User Reason and the Established Reason associated with the User Product, providing the User with a Dosage.

45. The system of claim 42, wherein the Attribute of the User Product is determined by a photo of the User Product, the photo compared with Products of the dynamic Database to identify at least one Constituent, at least one Established Reason, and a Dosage for the Established Reason correlating to the User Product, and in response to a correlation between the User Reason and the Established Reason associated with the User Product, providing the User with a Dosage.

46. The system of claim 35, wherein each Product further has a Use Rating for each Established Reason.

47. The system of claim 46, further including receiving from the User a Rating after use of a Chosen Product selected from the first subset of Products, and updating the User Rating for the Established Reason correlating to the User Reason of the Chosen Product.

48. The system of claim 35, wherein subsequent to use of a selected Product from the first subset of Products, the User using the at least one remote application to provide a quantified rank of effectiveness of the selected Product in alleviating the specified ailment, the Correlation Table adjusted by this feedback to further improve the correlation of the Established Reason to the Constituents of the selected Product.

49. The system of claim 35, wherein the initial correlation of the ratio of Constituents each Product to each Established Reason is established by User feedback providing quantified rank of effectiveness on the use of a selected Product for one of the Established Reasons.

* * * * *